United States Patent [19]

Olsson et al.

[11] Patent Number: 5,639,458

[45] Date of Patent: Jun. 17, 1997

[54] CLASS I MHC MODULATION OF SURFACE RECEPTOR ACTIVITY

[75] Inventors: Lennart Olsson, Orinda; Robert S. Goodenow, Coto de Casa; Avram Goldstein, Stanford, all of Calif.

[73] Assignee: Regents of the University of California, Alameda, Calif.

[21] Appl. No.: 105,416

[22] Filed: Aug. 12, 1993

Related U.S. Application Data

[63] Continuation-in-part of Ser. No. 57,184, May 3, 1993, Pat. No. 5,385,888, which is a continuation of Ser. No. 649,471, Feb. 1, 1991, abandoned, which is a continuation-in-part of Ser. No. 323,565, Mar. 14, 1989, abandoned, which is a continuation-in-part of Ser. No. 28,241, Mar. 20, 1987, abandoned.

[51] Int. Cl.$^6$ .......................... A61K 38/00; C07K 14/74
[52] U.S. Cl. .......................... 424/185.1; 514/2; 514/12; 514/16; 530/300; 530/324; 530/328; 530/868
[58] Field of Search .......................... 424/184.1, 185.1, 424/198.1; 514/2, 8, 12, 16; 530/300, 350, 395, 868, 324–328

[56] References Cited

U.S. PATENT DOCUMENTS 5,385,888  1/1995  Goodenow .......................... 514/12
5,516,642  5/1996  Mapelli .......................... 435/7.21

OTHER PUBLICATIONS

Stagsted, J., et al., Cell 62:297–307 (Jul. 27, 1990), "Regulation of Insulin Receptor Functions by a Peptide Derived From a Major Histocompatibility Complex Class I Antigen".

*Primary Examiner*—Thomas M. Cunningham
*Attorney, Agent, or Firm*—Townsend and Townsend and Crew LLP

[57] ABSTRACT

Methods and compositions are provided for regulating surface membrane receptor responses, where the surface membrane receptor is a glucose transporter, by modulating interaction between MHC Class I antigen and the surface membrane receptor. Various techniques may be employed for enhancing or reducing the interaction between the MHC Class I antigen and surface membrane receptor (e.g., enhancing surface expression of the MHC Class I antigen or employing agents which affect interaction between MHC Class I antigen and surface receptors). The aggregative characteristics of oligopeptides which act as agents in affecting interaction between MHC Class I antigen and surface receptors may be employed in a screening assay for determining drugs which affect interaction between Class I antigen and surface receptors. Active peptide aggregative characteristics may also be employed in a method of administration of effectors of surface receptor response modulation.

16 Claims, 7 Drawing Sheets

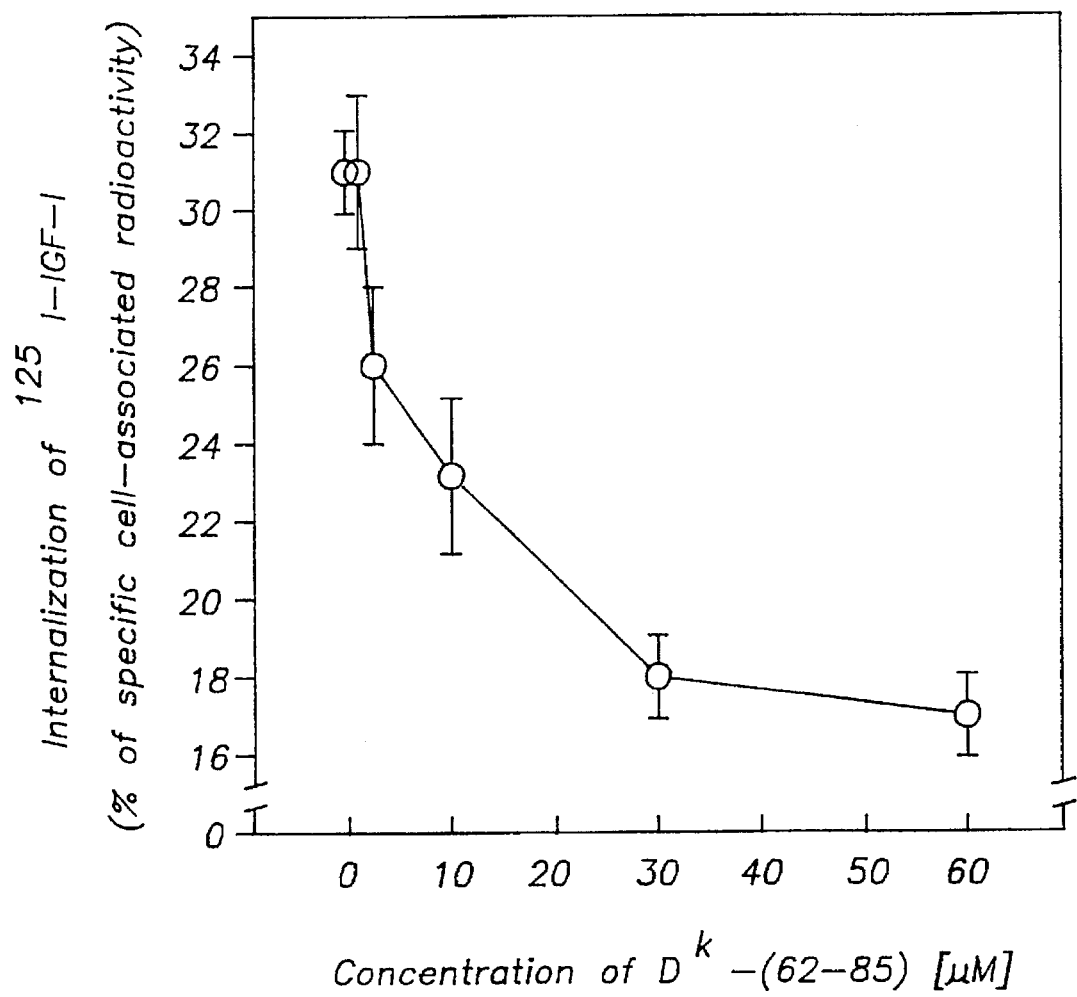
FIG.—5

SEQUENCE LISTING ( 1 ) GENERAL INFORMATION:

( i i i ) NUMBER OF SEQUENCES: 40

( 2 ) INFORMATION FOR SEQ ID NO:1:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 2
        ( D ) OTHER INFORMATION: /product="Xaa at position 2"
           / note= "Xaa at position 2 may be a neutral aliphatic
           amino acid of from 4 to 6 carbon atoms, particularly
           V, I, L, M"

( i x ) FEATURE:
        ( A ) NAME/KEY: Peptide
        ( B ) LOCATION: 5
        ( D ) OTHER INFORMATION: /note= "Xaa at position 5 may be an
           amino acid selected from K, R, D, and E"

( i x ) FEATURE:
        ( A ) NAME/KEY: Peptide
        ( B ) LOCATION: 6

(D) OTHER INFORMATION: /note= "Xaa at position 6 may be an
amino acid selected from D, E, K, and R."

(xi) SEQUENCE DESCRIPTION: SEQ ID NO:1:

Trp Xaa Glu Gln Xaa Xaa Gly Pro Glu Tyr Trp
1               5                   10

(2) INFORMATION FOR SEQ ID NO:2:

(i) SEQUENCE CHARACTERISTICS:
    (A) LENGTH: 13 amino acids
    (B) TYPE: amino acid
    (C) STRANDEDNESS: single
    (D) TOPOLOGY: linear (ii) MOLECULE TYPE: peptide (ix) FEATURE:
    (A) NAME/KEY: Peptide
    (B) LOCATION: 2
    (D) OTHER INFORMATION: /note= "Xaa at position 2 is D or
        E"

(ix) FEATURE:
    (A) NAME/KEY: Peptide
    (B) LOCATION: 3
    (D) OTHER INFORMATION: /note= "Xaa at position 3 is K, R,
        G or A"

(ix) FEATURE:
    (A) NAME/KEY: Peptide
    (B) LOCATION: 4
    (D) OTHER INFORMATION: /note= "Xaa at position 4 is D, E,
        I, L, V, N, or Q"

(ix) FEATURE:
    (A) NAME/KEY: Peptide
    (B) LOCATION: 6
    (D) OTHER INFORMATION: /note= "Xaa at position 6 is N, Q,
        K Or R"

(ix) FEATURE:
    (A) NAME/KEY: Peptide
    (B) LOCATION: 7
    (D) OTHER INFORMATION: /note= "Xaa at position 7 is L, I,
        V, K, R, N or Q"

(ix) FEATURE:
    (A) NAME/KEY: Peptide
    (B) LOCATION: 8
    (D) OTHER INFORMATION: /note= "Xaa at position 8 is G, A,
        L, V, I, S, T, M, C, F, Y, N or Q"

(ix) FEATURE:
    (A) NAME/KEY: Peptide
    (B) LOCATION: 10
    (D) OTHER INFORMATION: /note= "Xaa at position 10 is D, E,
        G, S, T or M"

(ix) FEATURE:
    (A) NAME/KEY: Peptide
    (B) LOCATION: 11
    (D) OTHER INFORMATION: /note= "Xaa at position 11 is N, Q,
        K, R, S or T"

(ix) FEATURE:
    (A) NAME/KEY: Peptide
    (B) LOCATION: 12
    (D) OTHER INFORMATION: /note= "Xaa at position 12 is
        selected from G, A, S, T, D, or E"

(xi) SEQUENCE DESCRIPTION: SEQ ID NO:2:

Trp Xaa Xaa Xaa Thr Xaa Xaa Xaa Lys Xaa Xaa Xaa Gln
1               5                   10

(2) INFORMATION FOR SEQ ID NO:3:

( i ) SEQUENCE CHARACTERISTICS:
    ( A ) LENGTH: 26 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Peptide
    ( B ) LOCATION: 2
    ( D ) OTHER INFORMATION: /note= "Xaa at position 2 is D or
        E"

( i x ) FEATURE:
    ( A ) NAME/KEY: Peptide
    ( B ) LOCATION: 3
    ( D ) OTHER INFORMATION: /note= "Xaa at position 3 is K, R,
        G, or A"

( i x ) FEATURE:
    ( A ) NAME/KEY: Peptide
    ( B ) LOCATION: 4
    ( D ) OTHER INFORMATION: /note= "Xaa at position 4 is D, E,
        I, L, V, N, or Q"

( i x ) FEATURE:
    ( A ) NAME/KEY: Peptide
    ( B ) LOCATION: 5
    ( D ) OTHER INFORMATION: /note= "Xaa at position 5 is S,T or
        M"

( i x ) FEATURE:
    ( A ) NAME/KEY: Peptide
    ( B ) LOCATION: 6
    ( D ) OTHER INFORMATION: /note= "Xaa at position 6 is N,Q,K
        or R"

( i x ) FEATURE:
    ( A ) NAME/KEY: Peptide
    ( B ) LOCATION: 7
    ( D ) OTHER INFORMATION: /note= "Xaa at position 7 is
        L,I,V,K,R,N or Q"

( i x ) FEATURE:
    ( A ) NAME/KEY: Peptide
    ( B ) LOCATION: 8
    ( D ) OTHER INFORMATION: /note= "Xaa at position 8 is
        G,A,L,V,I,S,T,M,C,F,Y,N,or Q"

( i x ) FEATURE:
    ( A ) NAME/KEY: Peptide
    ( B ) LOCATION: 10
    ( D ) OTHER INFORMATION: /note= "Xaa at position 10 is
        D,E,G,S,T or M"

( i x ) FEATURE:
    ( A ) NAME/KEY: Peptide
    ( B ) LOCATION: 11
    ( D ) OTHER INFORMATION: /note= "Xaa at position 11 is
        N,Q,K,R,S,or T"

( i x ) FEATURE:
    ( A ) NAME/KEY: Peptide
    ( B ) LOCATION: 12
    ( D ) OTHER INFORMATION: /note= "Xaa at position 12 is
        G,A,S,T,D,or E"

( i x ) FEATURE:
    ( A ) NAME/KEY: Peptide
    ( B ) LOCATION: 13
    ( D ) OTHER INFORMATION: /note= "Xaa at position 13 is
        selected from N or Q"

( i x ) FEATURE:
    ( A ) NAME/KEY: Peptide
    ( B ) LOCATION: 14
    ( D ) OTHER INFORMATION: /note= "Xaa at position 14 is
        S,T,F,Y,H or W"

( i x ) FEATURE:
  ( A ) NAME/KEY: Peptide
  ( B ) LOCATION: 15
  ( D ) OTHER INFORMATION: /note= "Xaa at position 15 is
        F,Y,H,or W"

( i x ) FEATURE:
  ( A ) NAME/KEY: Peptide
  ( B ) LOCATION: 16
  ( D ) OTHER INFORMATION: /note= "Xaa at position 16 is K or
        R"

( i x ) FEATURE:
  ( A ) NAME/KEY: Peptide
  ( B ) LOCATION: 17
  ( D ) OTHER INFORMATION: /note= "Xaa at position 17 is
        D,E,V,I,or L"

( i x ) FEATURE:
  ( A ) NAME/KEY: Peptide
  ( B ) LOCATION: 18
  ( D ) OTHER INFORMATION: /note= "Xaa at position 18 is
        N,Q,S,T,D,or E"

( i x ) FEATURE:
  ( A ) NAME/KEY: Peptide
  ( B ) LOCATION: 19
  ( D ) OTHER INFORMATION: /note= "Xaa at position 19 is
        A,P,V,I or L"

( i x ) FEATURE:
  ( A ) NAME/KEY: Peptide
  ( B ) LOCATION: 20
  ( D ) OTHER INFORMATION: /note= "Xaa at position 20 is K or
        R"

( i x ) FEATURE:
  ( A ) NAME/KEY: Peptide
  ( B ) LOCATION: 21
  ( D ) OTHER INFORMATION: /note= "Xaa at position 21 is any
        neutral amino acid other than A, particularly S,T,N,Q,I,
        V,or L"

( i x ) FEATURE:
  ( A ) NAME/KEY: Peptide
  ( B ) LOCATION: 22
  ( D ) OTHER INFORMATION: /note= "Xaa at position 22 is an
        aliphatic non-polar amino acid other than A,
        particularly G,L,I or V"

( i x ) FEATURE:
  ( A ) NAME/KEY: Peptide
  ( B ) LOCATION: 23
  ( D ) OTHER INFORMATION: /note= "Xaa at position 23 is
        K,R,G,L,I or V"

( i x ) FEATURE:
  ( A ) NAME/KEY: Peptide
  ( B ) LOCATION: 24
  ( D ) OTHER INFORMATION: /note= "Xaa at position 24 is
        K,R,G,L,I or V"

( i x ) FEATURE:
  ( A ) NAME/KEY: Peptide
  ( B ) LOCATION: 25
  ( D ) OTHER INFORMATION: /note= "Xaa at position 25 is
        F,Y,H,or W"

( i x ) FEATURE:
  ( A ) NAME/KEY: Peptide
  ( B ) LOCATION: 26
  ( D ) OTHER INFORMATION: /note= "Xaa at position 26 is
        F,Y,H,or W"

( x i ) SEQUENCE DESCRIPTION: SEQ ID NO:3:

Trp Xaa Xaa Xaa Xaa Xaa Xaa Xaa Lys Xaa Xaa Xaa Xaa Xaa Xaa
1               5                   10                  15

```
Xaa Xaa Xaa Xaa Xaa Xaa Xaa Xaa Xaa Xaa
         20                      25
```

(2) INFORMATION FOR SEQ ID NO:4:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 5
        (D) OTHER INFORMATION: /note= "Xaa at position 5 is
            S,T,F,Y,H or W"

(ix) FEATURE:
        (A) NAME/KEY: Peptide
        (B) LOCATION: 6
        (D) OTHER INFORMATION: /note= "Xaa at position 6 is
            F,Y,H, or W"

(ix) FEATURE:
        (A) NAME/KEY: Peptide
        (B) LOCATION: 9
        (D) OTHER INFORMATION: /note= "Xaa at position 9 is
            N,Q,S,T,D, or E"

(ix) FEATURE:
        (A) NAME/KEY: Peptide
        (B) LOCATION: 10
        (D) OTHER INFORMATION: /note= "Xaa at position 10 is
            A,P,V,I or L"

(ix) FEATURE:
        (A) NAME/KEY: Peptide
        (B) LOCATION: 12
        (D) OTHER INFORMATION: /note= "Xaa at position 12 is
            S,T,N,Q,I,V or L"

(ix) FEATURE:
        (A) NAME/KEY: Peptide
        (B) LOCATION: 13
        (D) OTHER INFORMATION: /note= "Xaa at position 13 is G,L,I
            or V"

(ix) FEATURE:
        (A) NAME/KEY: Peptide
        (B) LOCATION: 14
        (D) OTHER INFORMATION: /note= "Xaa at position 14 is
            K,R,G,L,I or V"

(ix) FEATURE:
        (A) NAME/KEY: Peptide
        (B) LOCATION: 17
        (D) OTHER INFORMATION: /note= "Xaa at position 17 is
            F,Y,H, or W"

(xi) SEQUENCE DESCRIPTION: SEQ ID NO:4:

```
Gly Asn Glu Gln Xaa Xaa Arg Val Xaa Xaa Arg Xaa Xaa Xaa Arg Tyr
1               5                   10                  15

Xaa
```

(2) INFORMATION FOR SEQ ID NO:5:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide ( i x ) FEATURE:
    ( A ) NAME/KEY: Peptide
    ( B ) LOCATION: 2
    ( D ) OTHER INFORMATION: /note= "Xaa at position 2 is D or
        E"

( i x ) FEATURE:
    ( A ) NAME/KEY: Peptide
    ( B ) LOCATION: 4
    ( D ) OTHER INFORMATION: /note= "Xaa at position 4 is E,I or
        N"

( i x ) FEATURE:
    ( A ) NAME/KEY: Peptide
    ( B ) LOCATION: 6
    ( D ) OTHER INFORMATION: /note= "Xaa at position 6 is Q or
        R"

( i x ) FEATURE:
    ( A ) NAME/KEY: Peptide
    ( B ) LOCATION: 7
    ( D ) OTHER INFORMATION: /note= "Xaa at position 7 is I,N,or
        K"

( i x ) FEATURE:
    ( A ) NAME/KEY: Peptide
    ( B ) LOCATION: 8
    ( D ) OTHER INFORMATION: /note= "Xaa at position 8 is
        A,C,S,M or Y"

( i x ) FEATURE:
    ( A ) NAME/KEY: Peptide
    ( B ) LOCATION: 10
    ( D ) OTHER INFORMATION: /note= "Xaa at position 10 is G,A,T
        or P"

( i x ) FEATURE:
    ( A ) NAME/KEY: Peptide
    ( B ) LOCATION: 11
    ( D ) OTHER INFORMATION: /note= "Xaa at position 11 is Q,N
        or K"

( i x ) FEATURE:
    ( A ) NAME/KEY: Peptide
    ( B ) LOCATION: 12
    ( D ) OTHER INFORMATION: /note= "Xaa at position 12 is A,E
        or T"

( i x ) FEATURE:
    ( A ) NAME/KEY: Peptide
    ( B ) LOCATION: 14
    ( D ) OTHER INFORMATION: /product="Xaa at position 14 is
        T,W or S"

( i x ) FEATURE:
    ( A ) NAME/KEY: Peptide
    ( B ) LOCATION: 17
    ( D ) OTHER INFORMATION: /note= "Xaa at position 17 is V or
        E"

( i x ) FEATURE:
    ( A ) NAME/KEY: Peptide
    ( B ) LOCATION: 18
    ( D ) OTHER INFORMATION: /note= "Xaa at position 18 is N,S
        or D"

( i x ) FEATURE:
    ( A ) NAME/KEY: Peptide
    ( B ) LOCATION: 21
    ( D ) OTHER INFORMATION: /note= "Xaa at position 21 is
        I,N,or T"

( i x ) FEATURE:
    ( A ) NAME/KEY: Peptide
    ( B ) LOCATION: 22
    ( D ) OTHER INFORMATION: /note= "Xaa at position 22 is L or
        A"

( i x ) FEATURE:
    ( A ) NAME/KEY: Peptide ( B ) LOCATION: 23
( D ) OTHER INFORMATION: /note= "Xaa at position 23 is L or
R"

( i x ) FEATURE:
( A ) NAME/KEY: Peptide
( B ) LOCATION: 24
( D ) OTHER INFORMATION: /note= "Xaa at position 24 is G or
R"

( i x ) FEATURE:
( A ) NAME/KEY: Peptide
( B ) LOCATION: 26
( D ) OTHER INFORMATION: /note= "Xaa at position 26 is any
amino acid, preferably Y or A."

( x i ) SEQUENCE DESCRIPTION: SEQ ID NO:5:

Trp Xaa Arg Xaa Thr Xaa Xaa Xaa Lys Xaa Xaa Xaa Gln Xaa Phe Arg
1               5                       10                      15

Xaa Xaa Leu Arg Xaa Xaa Xaa Xaa Tyr Xaa
            20                  25

( 2 ) INFORMATION FOR SEQ ID NO:6:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Peptide
( B ) LOCATION: 1
( D ) OTHER INFORMATION: /note= "Xaa at position 1 is N or
Q"

( i x ) FEATURE:
( A ) NAME/KEY: Peptide
( B ) LOCATION: 2
( D ) OTHER INFORMATION: /note= "Xaa at position 2 is S or
T"

( i x ) FEATURE:
( A ) NAME/KEY: Peptide
( B ) LOCATION: 3
( D ) OTHER INFORMATION: /note= "Xaa at position 3 is F,Y or
W"

( i x ) FEATURE:
( A ) NAME/KEY: Peptide
( B ) LOCATION: 4
( D ) OTHER INFORMATION: /note= "Xaa at position 4 is any
non-acidic aliphatic amino acid other than A"

( i x ) FEATURE:
( A ) NAME/KEY: Peptide
( B ) LOCATION: 5
( D ) OTHER INFORMATION: /note= "Xaa at position 5 is K or
R"

( i x ) FEATURE:
( A ) NAME/KEY: Peptide
( B ) LOCATION: 6
( D ) OTHER INFORMATION: /note= "Xaa at position 6 is N,S,or
D"

( i x ) FEATURE:
( A ) NAME/KEY: Peptide
( B ) LOCATION: 7
( D ) OTHER INFORMATION: /note= "Xaa at position 7 is any
non-acidic aliphatic amino acid other than A"

( i x ) FEATURE:
( A ) NAME/KEY: Peptide
( B ) LOCATION: 8

(D) OTHER INFORMATION: /note= "Xaa at position 8 is K or R"

(ix) FEATURE:
    (A) NAME/KEY: Peptide
    (B) LOCATION: 9
    (D) OTHER INFORMATION: /note= "Xaa at position 9 is S or T"

(ix) FEATURE:
    (A) NAME/KEY: Peptide
    (B) LOCATION: 10
    (D) OTHER INFORMATION: /note= "Xaa at position 10 is I,L or T"

(ix) FEATURE:
    (A) NAME/KEY: Peptide
    (B) LOCATION: 11
    (D) OTHER INFORMATION: /note= "Xaa at position 11 is I,L or T"

(xi) SEQUENCE DESCRIPTION: SEQ ID NO:6:

```
Xaa Xaa Xaa Xaa Xaa Xaa Xaa Xaa Xaa Xaa Xaa
1               5                       10
```

(2) INFORMATION FOR SEQ ID NO:7:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Glu Arg Glu Thr Gln Ile Ala Lys Gly Asn Glu Gln Ser Phe Arg Val
1               5                   10                  15
Asp Leu Arg Thr Leu Leu Arg Tyr Tyr
            20              25
```

(2) INFORMATION FOR SEQ ID NO:8:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Asp Met Ala Ala Gln Ile Thr Arg Arg Lys Trp Glu Gln Ser Gly Ala
1               5                   10                  15
Ala Glu His Tyr Lys Ala Tyr Leu Glu
            20              25
```

(2) INFORMATION FOR SEQ ID NO:9:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ala Ala Glu His Tyr Lys Ala Tyr Leu Glu Gly Glu Cys Val Glu Trp
1               5                   10                  15
```

```
        Leu  His  Arg  Tyr  Leu  Lys  Asn  Gly  Asn
                  20                      25
```

( 2 ) INFORMATION FOR SEQ ID NO:10:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:10:

```
Gly  Glu  Val  Thr  Leu  Arg  Cys  Trp  Ala  Leu  Gly  Phe  Tyr  Pro  Ala  Asp
1              5                        10                       15

Ile  Thr  Leu  Thr  Trp  Gln  Leu  Asn  Gly
               20                       25
```

( 2 ) INFORMATION FOR SEQ ID NO:11:

( i ) SEQUENCE CHARACTERISTICS:
      ( A ) LENGTH: 24 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:11:

```
Arg  Glu  Thr  Gln  Ile  Ala  Lys  Gly  Asn  Glu  Gln  Ser  Phe  Arg  Val  Asp
1              5                        10                       15

Leu  Arg  Thr  Leu  Leu  Arg  Tyr  Tyr
               20
```

( 2 ) INFORMATION FOR SEQ ID NO:12:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:12:

```
Gly  Asn  Glu  Gln  Ser  Phe  Arg  Val  Asp  Leu  Arg  Thr  Leu  Leu  Arg  Tyr
1              5                        10                       15

Tyr
```

( 2 ) INFORMATION FOR SEQ ID NO:13:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:13:

```
Gly  Asn  Ala  Gln  Ser  Phe  Arg  Val  Asp  Leu  Arg  Thr  Leu  Leu  Arg  Tyr
1              5                        10                       15

Tyr
```

( 2 ) INFORMATION FOR SEQ ID NO:14:

( i ) SEQUENCE CHARACTERISTICS:
   ( A ) LENGTH: 24 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:14:

Arg Glu Thr Gln Ile Ala Lys Gly Asn Glu Gln Ser Ala Arg Val Asp
1               5                   10                  15

Leu Arg Thr Leu Leu Arg Tyr Tyr
            20

( 2 ) INFORMATION FOR SEQ ID NO:15:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:15:

Gly Asn Glu Gln Ser Phe Arg Val Asp Ala Arg Thr Leu Leu Arg Tyr
1               5                   10                  15

Tyr ( 2 ) INFORMATION FOR SEQ ID NO:16:

( i ) SEQUENCE CHARACTERISTICS:
      ( A ) LENGTH: 18 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:16:

Gly Asn Glu Gln Ser Phe Arg Val Asp Leu Arg Thr Leu Ala Leu Arg
1               5                   10                  15

Tyr Tyr ( 2 ) INFORMATION FOR SEQ ID NO:17:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:17:

Gly Asn Glu Gln Ser Phe Arg Val Asp Leu Arg Thr Leu Ala Arg Tyr
1               5                   10                  15

Tyr ( 2 ) INFORMATION FOR SEQ ID NO:18:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:18:

Gly Asn Glu Gln Ser Phe Arg Val Asp Leu Arg Thr Leu Leu Ala Tyr
1               5                   10                  15

Tyr ( 2 ) INFORMATION FOR SEQ ID NO:19:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Gly Asn Glu Gln Ser Phe Arg Val Asp Leu Arg Thr Leu Leu Arg Ala
1               5                   10                  15

Tyr ( 2 ) INFORMATION FOR SEQ ID NO:20:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Gly Asn Glu Gln Ser Phe Arg Val Asp Leu Arg Thr Leu Leu Arg Tyr
1               5                   10                  15

Ala ( 2 ) INFORMATION FOR SEQ ID NO:21:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

Arg Glu Thr Gln Ile Ala Ala Gly Asn Glu Gln Ser Phe Ala Val Asp
1               5                   10                  15

Leu Arg Thr Leu Leu Arg Tyr Tyr
                20

( 2 ) INFORMATION FOR SEQ ID NO:22:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

Arg Glu Thr Gln Ile Ala Lys Ala Asn Glu Gln Ser Phe Arg Ala Asp
1               5                   10                  15

Leu Arg Thr Leu Leu Arg Tyr Tyr ( 2 ) INFORMATION FOR SEQ ID NO:23:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Arg Glu Thr Gln Ile Ala Lys Gly Ala Glu Gln Ser Phe Arg Val Ala
1               5                   10                  15
Leu Arg Thr Leu Leu Arg Tyr Tyr
            20
```

( 2 ) INFORMATION FOR SEQ ID NO:24:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Arg Glu Thr Gln Ile Ala Lys Gly Asn Glu Ala Ser Phe Arg Val Asp
1               5                   10                  15
Leu Ala Thr Leu Leu Arg Tyr Tyr
            20
```

( 2 ) INFORMATION FOR SEQ ID NO:25:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Arg Glu Thr Gln Ile Ala Lys Gly Asn Glu Gln Ala Phe Arg Val Asp
1               5                   10                  15
Leu Arg Ala Leu Leu Arg Tyr Tyr
            20
```

( 2 ) INFORMATION FOR SEQ ID NO:26:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

```
Ala His Ser Gln Thr His Arg Val Asp Leu Gly Thr Leu Arg Gly Tyr
1               5                   10                  15
Tyr
```

( 2 ) INFORMATION FOR SEQ ID NO:27:

( i ) SEQUENCE CHARACTERISTICS:
   ( A ) LENGTH: 17 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:27:

Ala His Ser Gln Thr His Arg Val Asp Leu Arg Thr Leu Leu Arg Tyr
1               5                   10                  15
Tyr ( 2 ) INFORMATION FOR SEQ ID NO:28:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:28:

Gly Asn Glu Gln Ser Phe Arg Val Asp Leu Gly Thr Leu Arg Gly Tyr
1               5                   10                  15
Tyr ( 2 ) INFORMATION FOR SEQ ID NO:29:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:29:

Ala Lys Ala Gln Thr Asp Arg Glu Asp Leu Arg Thr Leu Leu Arg Tyr
1               5                   10                  15
Tyr ( 2 ) INFORMATION FOR SEQ ID NO:30:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:30:

Ala Lys Ala Gln Thr Phe Arg Glu Asp Leu Arg Thr Leu Leu Arg Tyr
1               5                   10                  15
Tyr ( 2 ) INFORMATION FOR SEQ ID NO:31:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:31:

Glu Arg Glu Thr Gln Ile Ala Lys Gly Asn Glu Gln Ser Phe Arg Val
1               5                       10                      15

Asp Leu Arg Thr Leu Leu Arg Tyr Tyr
            20              25

( 2 ) INFORMATION FOR SEQ ID NO:32:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 3
        ( D ) OTHER INFORMATION: /note= "Xaa at position 3 is G, A,
            S, T, D or E"

( i x ) FEATURE:
        ( A ) NAME/KEY: Region
        ( B ) LOCATION: 5
        ( D ) OTHER INFORMATION: /note= "Xaa at position 5 is
            S,T,F,Y,H or W"

( i x ) FEATURE:
        ( A ) NAME/KEY: Region
        ( B ) LOCATION: 8
        ( D ) OTHER INFORMATION: /note= "Xaa at position 8 is an
            aliphatic amino acid other than basic of from 4 to 6
            carbon atoms or A"

( i x ) FEATURE:
        ( A ) NAME/KEY: Region
        ( B ) LOCATION: 9
        ( D ) OTHER INFORMATION: /note= "Xaa at position 9 is a
            polar aliphatic amino acid of from 3 to 6 carbon atoms
            or A"

( i x ) FEATURE:
        ( A ) NAME/KEY: Region
        ( B ) LOCATION: 10
        ( D ) OTHER INFORMATION: /note= "Xaa at position 10 is a
            non-polar aliphatic amino acid of from 3 to 6 carbon
            atoms"

( i x ) FEATURE:
        ( A ) NAME/KEY: Region
        ( B ) LOCATION: 13
        ( D ) OTHER INFORMATION: /note= "Xaa at position 13 is G,L,I
            or V"

( i x ) FEATURE:
        ( A ) NAME/KEY: Region
        ( B ) LOCATION: 17
        ( D ) OTHER INFORMATION: /note= "Xaa at position 17 is an
            amino group to provide an amide terminal group, or the
            amino acids alanine or tyrosine terminating in a carboxy
            group"

( x i ) SEQUENCE DESCRIPTION: SEQ ID NO:32:

Gly Asn Xaa Gln Xaa Phe Arg Xaa Xaa Xaa Arg Thr Xaa Leu Arg Tyr
1               5                       10                      15

Xaa ( 2 ) INFORMATION FOR SEQ ID NO:33:

( i ) SEQUENCE CHARACTERISTICS:
        ( A ) LENGTH: 17 amino acids
        ( B ) TYPE: amino acid
        ( C ) STRANDEDNESS: single (D) TOPOLOGY: linear (i i) MOLECULE TYPE: peptide (i x) FEATURE:
 (A) NAME/KEY: Region
 (B) LOCATION: 5
 (D) OTHER INFORMATION: /note= "Xaa at position 5 is
  S,T,F,Y,H or W"

(i x) FEATURE:
 (A) NAME/KEY: Region
 (B) LOCATION: 8
 (D) OTHER INFORMATION: /note= "Xaa at position 8 is an
  aliphatic amino acid other than basic of from 4 to 6
  carbon atoms"

(i x) FEATURE:
 (A) NAME/KEY: Region
 (B) LOCATION: 9
 (D) OTHER INFORMATION: /note= "Xaa at position 9 is a
  polar aliphatic amino acid of from 3 to 6 carbon atoms"

(i x) FEATURE:
 (A) NAME/KEY: Region
 (B) LOCATION: 10
 (D) OTHER INFORMATION: /note= "Xaa at position 10 is a
  neutral aliphatic amino acid of from 5 to 6 carbon atoms"

(i x) FEATURE:
 (A) NAME/KEY: Region
 (B) LOCATION: 13
 (D) OTHER INFORMATION: /note= "Xaa at position 13 is G,L,I
  or V"

(i x) FEATURE:
 (A) NAME/KEY: Region
 (B) LOCATION: 17
 (D) OTHER INFORMATION: /note= "Xaa at position 17 is an
  amino group to provide an amide terminal group, or the
  amino acids alanine or tyrosine terminating in a carboxy
  group"

(x i) SEQUENCE DESCRIPTION: SEQ ID NO:33:

```
Gly  Asn  Glu  Gln  Xaa  Phe  Arg  Xaa  Xaa  Xaa  Arg  Thr  Xaa  Leu  Arg  Tyr
 1                  5                        10                      15

Xaa
```

(2) INFORMATION FOR SEQ ID NO:34:

(i) SEQUENCE CHARACTERISTICS:
  (A) LENGTH: 26 amino acids
  (B) TYPE: amino acid
  (C) STRANDEDNESS: single
  (D) TOPOLOGY: linear (i i) MOLECULE TYPE: peptide (i x) FEATURE:
  (A) NAME/KEY: Region
  (B) LOCATION: 2
  (D) OTHER INFORMATION: /note= "Xaa at position 2 is D or
   E"

(i x) FEATURE:
  (A) NAME/KEY: Region
  (B) LOCATION: 4
  (D) OTHER INFORMATION: /note= "Xaa at position 4 is E, I
   or N"

(i x) FEATURE:
  (A) NAME/KEY: Region
  (B) LOCATION: 6
  (D) OTHER INFORMATION: /note= "Xaa at position 6 is Q or
   R"

(i x) FEATURE:

(A) NAME/KEY: Region
(B) LOCATION: 7
(D) OTHER INFORMATION: /note= "Xaa at position 7 is I,N or K"

(ix) FEATURE:
(A) NAME/KEY: Region
(B) LOCATION: 8
(D) OTHER INFORMATION: /note= "Xaa at position 8 is A,C,S or M"

(ix) FEATURE:
(A) NAME/KEY: Region
(B) LOCATION: 10
(D) OTHER INFORMATION: /note= "Xaa at position 10 is G,A,T or P"

(ix) FEATURE:
(A) NAME/KEY: Region
(B) LOCATION: 11
(D) OTHER INFORMATION: /note= "Xaa at position 11 is N,Q,K,R,S or T"

(ix) FEATURE:
(A) NAME/KEY: Region
(B) LOCATION: 12
(D) OTHER INFORMATION: /note= "Xaa at position 12 is G,A,S,T,D or E"

(ix) FEATURE:
(A) NAME/KEY: Region
(B) LOCATION: 14
(D) OTHER INFORMATION: /note= "Xaa at position 14 is S,T or W"

(ix) FEATURE:
(A) NAME/KEY: Region
(B) LOCATION: 17
(D) OTHER INFORMATION: /note= "Xaa at position 17 is V or E"

(ix) FEATURE:
(A) NAME/KEY: Region
(B) LOCATION: 18
(D) OTHER INFORMATION: /note= "Xaa at position 18 is N, S or D"

(ix) FEATURE:
(A) NAME/KEY: Region
(B) LOCATION: 23
(D) OTHER INFORMATION: /note= "Xaa at position 23 is L or R"

(ix) FEATURE:
(A) NAME/KEY: Region
(B) LOCATION: 24
(D) OTHER INFORMATION: /note= "Xaa at position 24 is G or R"

(ix) FEATURE:
(A) NAME/KEY: Region
(B) LOCATION: 26
(D) OTHER INFORMATION: /note= "Xaa at position 26 is Y or A"

(xi) SEQUENCE DESCRIPTION: SEQ ID NO:34:

```
Trp Xaa Arg Xaa Thr Xaa Xaa Xaa Lys Xaa Xaa Xaa Gln Xaa Phe Arg
1               5                   10                  15
Xaa Xaa Leu Arg Thr Leu Xaa Xaa Tyr Xaa
            20              25
```

(2) INFORMATION FOR SEQ ID NO:35:

(i) SEQUENCE CHARACTERISTICS:
(A) LENGTH: 26 amino acids
(B) TYPE: amino acid
(C) STRANDEDNESS: single (D) TOPOLOGY: linear (i i) MOLECULE TYPE: peptide (i x) FEATURE:
 (A) NAME/KEY: Region
 (B) LOCATION: 4
 (D) OTHER INFORMATION: /note= "Xaa at position 4 is E or I"

(i x) FEATURE:
 (A) NAME/KEY: Region
 (B) LOCATION: 11
 (D) OTHER INFORMATION: /note= "Xaa at position 11 is N or Q"

(i x) FEATURE:
 (A) NAME/KEY: Region
 (B) LOCATION: 14
 (D) OTHER INFORMATION: /note= "Xaa at position 14 is S or W"

(i x) FEATURE:
 (A) NAME/KEY: Region
 (B) LOCATION: 18
 (D) OTHER INFORMATION: /note= "Xaa at position 18 id D or N"

(x i) SEQUENCE DESCRIPTION: SEQ ID NO:35:

Trp Glu Arg Xaa Thr Gln Ile Ala Lys Gly Xaa Glu Gln Xaa Phe Arg
1               5                   10                  15

Val Xaa Leu Arg Thr Leu Leu Arg Tyr Tyr
        20                  25

(2) INFORMATION FOR SEQ ID NO:36:

(i) SEQUENCE CHARACTERISTICS:
  (A) LENGTH: 7 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:36:

Leu Arg Thr Leu Leu Arg Tyr
1               5

(2) INFORMATION FOR SEQ ID NO:37:

(i) SEQUENCE CHARACTERISTICS:
  (A) LENGTH: 17 amino acids
  (B) TYPE: amino acid
  (C) STRANDEDNESS: single
  (D) TOPOLOGY: linear (i i) MOLECULE TYPE: peptide (i x) FEATURE:
  (A) NAME/KEY: Region
  (B) LOCATION: 17
  (D) OTHER INFORMATION: /note= "Xaa at position 17 is an amino group to provide an amide terminal group, or the amino acids alanine or tyrosine terminating in a carboxy group"

(x i) SEQUENCE DESCRIPTION: SEQ ID NO:37:

Gly Asn Glu Gln Ser Phe Arg Val Asp Leu Arg Thr Leu Leu Arg Tyr
1               5                   10                  15

Xaa (2) INFORMATION FOR SEQ ID NO:38:

( i ) SEQUENCE CHARACTERISTICS:
  ( A ) LENGTH: 17 amino acids
  ( B ) TYPE: amino acid
  ( C ) STRANDEDNESS: single
  ( D ) TOPOLOGY: linear ( i i ) MOLECULE TYPE: peptide ( i x ) FEATURE:
  ( A ) NAME/KEY: Region
  ( B ) LOCATION: 17
  ( D ) OTHER INFORMATION: /note= "Xaa at position 17 is an amino group to provide an amide terminal group or the amino acids alanine or tyrosine terminating in a carboxy group"

( x i ) SEQUENCE DESCRIPTION: SEQ ID NO:38:

Gly Asn Ala Gln Ser Phe Arg Val Asp Leu Arg Thr Leu Leu Arg Tyr
1               5                   10                  15
Xaa ( 2 ) INFORMATION FOR SEQ ID NO:39:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 17
    ( D ) OTHER INFORMATION: /note= "Xaa at position 17 is an amino group to provide an amide terminal group or the amino acids alanine or tyrosine terminating in a carboxy group"

( x i ) SEQUENCE DESCRIPTION: SEQ ID NO:39:

Gly Asn Glu Gln Ser Phe Arg Val Asp Ala Arg Thr Leu Leu Arg Tyr
1               5                   10                  15
Xaa ( 2 ) INFORMATION FOR SEQ ID NO:40:

( i ) SEQUENCE CHARACTERISTICS:
    ( A ) LENGTH: 17 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 17
    ( D ) OTHER INFORMATION: /note= "Xaa at position 17 is an amino group to provide an amide terminal group or the amino acids alanine or tyrosine terminating in a carboxy group."

( x i ) SEQUENCE DESCRIPTION: SEQ ID NO:40:

Gly Asn Glu Gln Ser Phe Arg Val Asp Leu Arg Thr Ala Leu Arg Tyr
1               5                   10                  15
Xaa

CLASS I MHC MODULATION OF SURFACE RECEPTOR ACTIVITY

This application is a continuation-in-part of application Ser. No. 08/057,184 filed May 3, 1993, now U.S. Pat. No. 5,385,888, which is a continuation of application Ser. No. 07/649,471 filed Feb. 1, 1991, now abandoned, which is a continuation-in-part of application Ser. No. 07/323,565 filed Mar. 14, 1989, which is a continuation-in-part of application Ser. No. 07/028,241 filed Mar. 20, 1987, now abandoned.

TECHNICAL FIELD

The field of the subject invention concerns modulation of surface membrane receptor responses.

BACKGROUND

The major histocompatibility complex (MHC) Class I antigens are expressed on virtually all types of vertebrate cells examined. These highly polymorphic transmembrane glycoproteins have a 45 kD heavy chain consisting of a short cytoplasmic C-terminal tail, a transmembrane region, and an extracellular N-terminal sequence which encompasses three domains ($\alpha_1$, $\alpha_2$, and $\alpha_3$). $\alpha_1$ and $\alpha_2$-domains carry all the immunological polymorphism, while the membrane-proximal $\alpha_3$ domain is non-covalently associated with the 12 kD $\beta_2$ microglobulin.

The MHC Class I antigen plays an essential role in restriction of the target cell repertoire of cytotoxic T-lymphocytes (CTL). Restriction involves preferential utilization of the different polymorphic MHC Class I antigens, H-2K, -D or -L (for mouse) or HLA-A, -B, or -C (for human), e.g. in recognition of virally infected cells. For the most part, attention has been directed to the role of the MHC Class I antigens in restricting T-cell activity. However, in addition to restriction of the immune response, Class I MHC antigens may also interact with receptors expressed on the cell surface.

RELEVANT LITERATURE

For a review of biological functions of MHC Class I antigens see Ohno, *Immunol. Rev.* (1977) 33:59–69; and Simonsen, *Prog. Allergy* (1985) 36:151–176. For a description of the insulin receptor see Cuatrecasas, *J. Biol. Chem.* (1972) 247:1980–1991; Kasuga et al., ibid. (1983) 258:10392–10399; and Kasuga et al., ibid. (1983) 258:10973–10980. For suggestion that Class I antigens and insulin receptors interact, see Olsson, In *Cell Fusion: Gene Transfer and Transformation* (eds. Beers & Bassett) 395–403 (Raven Press, New York, 1984); Simonsen and Olsson, *Ann. Immunol.* (1983) 134D:85–92; and Stagsted, et al. *Cell* (1990) 62:297–307. Other evidence supporting the interaction between MHC products and insulin receptor may be found in Fehlman et al., Phillips et al., ibid (1986) 86:3474–3478; Due et al., ibid. (1986) 83:6007–6001, and Samson et al., *J. Immunology* (1986) 137:2293–2298. Evidence for the inhibition of insulin receptor phosphorylation by MHC Class I peptides can be found in Hansen, et al. *Proc. Natl. Acad. Sci. USA* (1989) 86:3123–3126. Suggestions of a correlation between over-expression of certain Class I products and increased metastatic potential of particular tumors may be found in Wallich et al., *Nature* (1985) 315:301–305; Katzav et al., *Int. J. Cancer* (1984) 33:47–415; Olsson, *Cancer Rev.* (1986) 3:91–114; and Goodenow et al., *Science* (1985) 230:777–783.

A structural association between epidermal growth factor receptor (EGFR) and MHC Class I on human cells has been suggested by Schreiber et al., *J. Cell Biol.* (1984) 98:725–731 and Phillips et al., *Proc. Natl. Acad. Sci. USA* (1986) 83:3474–3478. The effect of MHC Class I peptides on glucose transport mediated by EGFR can be found in Stagsted, et al. *J. Biol. Chem.* (1993) 268(3):1770–1774. A review of EGFR and its functions may be Found in Carpenter and Cohen, *Ann. Rev. Biochem.* (1979) 48:193–216 and Carpenter, *J. Cell Sci. Suppl.* (1985) 3:1–9.

Other receptors of interest and appropriate references of relevance to these receptors include: IGF-I, Rosen *Science* (1987) 237:1452–1458; IGF-II, Simpson and Cushman Ann. *Rev. Biochem.* (1986) 55:1059–1089; LDL receptor, Hobbs, et al. Human Mutat. (1992) 1:445–466; scavenger LDL receptor, Krieger, et al. *J. Biol. Chem.* (1993) 268:4569–4572; and $\beta_2$-andrenergic receptor, Pitcher, et al. *Science* (1992) 257:1264–1267.

SUMMARY OF THE INVENTION

Methods and compositions are provided for modulating the activity of cell surface receptors. The methods of the subject invention may employ tip or down regulation of MHC Class I antigens to modulate surface expression of receptors. Alternatively, the methods of the subject invention may modulate surface expression of surface receptors by employing substances which arc agonistic or antagonistic to the interactions between MHC Class I antigen, surface receptors or other molecules which mediate surface receptor internalization. The methods and compositions of the subject invention may be used in diagnosis and therapy of diseases which involve inadequate or inappropriate receptor response as well as in the screening of drug candidates which may affect surface expression of receptors.

BRIEF DESCRIPTION OF THE DRAWINGS

FIG. 5. Internalization of bound $^{125}$I-IGF-I to chinese hamster ovary cells as a function of increasing $D^k$-(65-85) peptide concentration.

DESCRIPTION OF SPECIFIC EMBODIMENTS

Figures 1A, 1B, 1C:
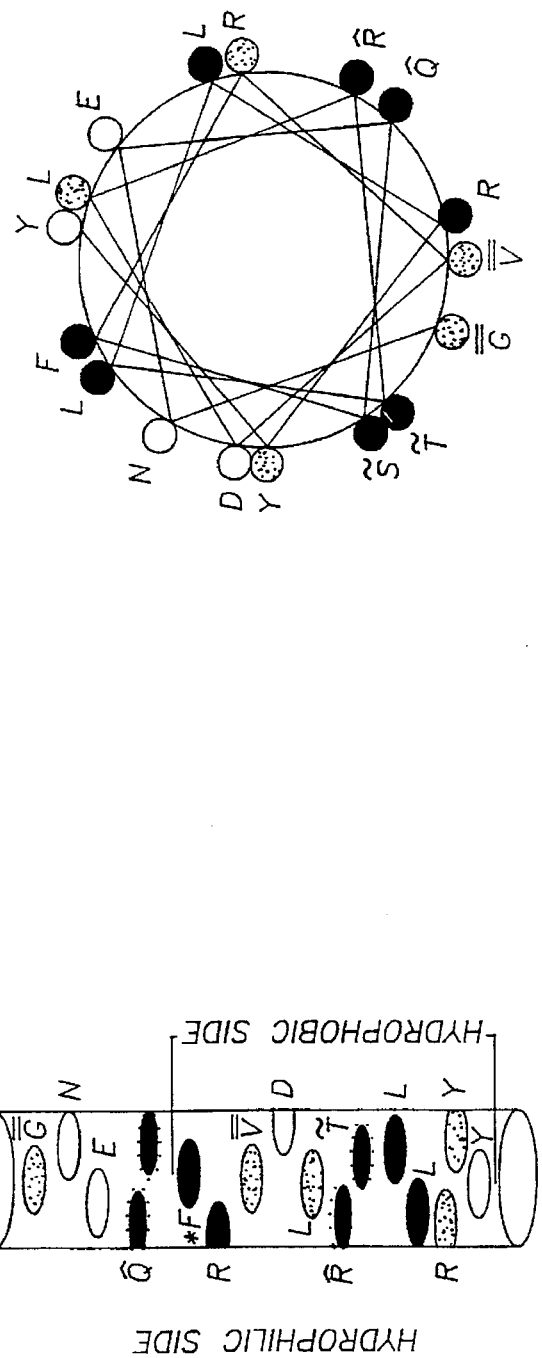
FIGS. 1A, B and C. Summary of relevance of each residue in $D^k$-(69-85) for biological activity, (insulin-stimulated glucose transport in rat adipose cells) and ordered structure in the MHC Class I peptides. In panel A, open circles indicate residues where substitution with alanine has no effect on activity; shaded circles indicate residues, which when substituted with alanine, result in reduced activity; solid circles indicate residues, which when substituted with alanine, result in complete loss of activity; ^, ~ and = indicate residues, which when simultaneously substituted with alanine, result in complete loss of activity; and * indicates a residue, which when substituted with alanine, results in loss of ordered structure and therefore complete loss of activity. Panel B depicts the helical rod of the peptide. Symbols encircled by a solid line or a dotted line indicate that the residue is localized on the front or back of the rod, respectively. Panel C depicts the helical rod of the peptide as viewed on end.

Methods and compositions are provided for modulating the response of cell surface receptors by affecting the interaction between the cell surface receptor and major histocompatibility (MHC) Class I antigen which in turn affects the surface expression of the receptor. Surface expression of receptors as used herein is intended to mean the appearance of the receptors at the cell surface. Thus, an increase in surface expression of a receptor results in an increase in the population of receptors on the cell surface. Modulation of surface expression of receptors, and thus the biological activity of the receptors, may be achieved through up or down regulation of Class I antigen surface expression or surface translocation. Alternatively, surface expression of receptors may be achieved by providing agents which may act as agonists or antagonists affecting the ability of Class I MHC to mediate receptor internalization or the susceptibility of the receptor to such internalization mediated by Class I MHC antigen Agents which may act as such agonists or antagonists may include oligopeptides, antibodies and the like. As the precise mechanism whereby MHC Class I antigens and agonistic or antagonistic agents modulate surface receptors is unknown, reference to interactions between MHC antigens, agents and receptors are intended to include direct binding between any of these molecules as well as indirect interactions, such as those mediated through other potential, though yet unidentified, accessory molecules. Modulation of the Class I antigen-receptor interaction can be used in diagnosing and treating a large variety of conditions associated with cellular membrane receptors.

MHC Class I antigens include human MHC Class I antigens and mammalian equivalents thereof, such as Class I antigens of the H-2 locus of mice, in particular H-2 D and K. Human MHC Class I antigens include, for example, HLA-A, B, C, Qa and T1. Of particular interest in the modulation of cellular receptors are the $\alpha_1$- and $\alpha_2$-domains of MHC Class I antigens, more particularly the $\alpha_1$-domain. Of more particular interest are the amino acid sequences involved in the polymorphic regions of $\alpha_1$- and $\alpha_2$-, ranging from amino acid 50 to amino acid 90, more particularly amino acids 55 to 90, usually 60 to 90, more particularly 62 to 90 or 90 to 120, more usually 90 to 116, where the amino acid sequences of interest are usually in the C-terminus of the $\alpha_1$-domain and N-terminus of the $\alpha_2$-domain. The region 60-85 of the $\alpha_1$-domain, more particularly 62 to 85 or 72–82 are found to be of particular interest. Regions of the $\alpha_2$-domain of particular interest are amino acids 72–75 separated by 2 to 4 amino acids from amino acids 79–82.

It is found that the amino acids from 83 to 85 of the native MHC Class I antigens are of interest. For both MHC Class I D and K, or analogous HLA-B or C, the sequence is R Y Y. Peptides derived from the native MHC sequence of interest may comprise, desirably at their C-terminal end, the sequence R Y Y, desirably R Y X, where X may be any amino acid, particularly alanine, or the chemical group $NH_2$ or other amino derivative. Peptides derived from the native MHC sequence of interest may include at least about 20, usually at least about 15, and preferably not more than about 10 amino acids on either side of the sequences indicated above, desirably having at least 5 amino acids at the N-terminal side, and more desirably not having more than about 5- amino acids at the C-terminal side of the native sequence. Desirably, the total number of amino acids will not exceed 24, preferably will not exceed about 18 with the sequences indicated above. Increasing the extent of the sequence does not significantly affect the activity, but rather primarily affects the ability to synthesize such peptides and to provide additional characteristics such as solubility, stability, and the like.

Also of interest is the region from about amino acid 30 to amino acid 45, more particularly 32 to 40, particularly an oligopeptide of at least four amino acids, more usually at least about six amino acids, and preferably at least about eight amino acids, where the sequence includes a tetramer involving an acidic amino acid and a basic amino acid separated by one neutral amino acid, particularly a neutral amino acid of at least five carbon atoms and one of the acidic or basic amino acids is flanked by a neutral amino acid. Of particular interest is where the intervening neutral amino acid is an aromatic or aliphatic hydrocarbon amino acid, e.g. glycine or phenylalanine.

A large number of surface membrane proteins are involved with the transduction of signals and serve as receptors for a wide variety of ligands. For the most part, receptors are defined by the ligand which activates the receptor for transduction or serves to endocytose the ligand. These receptors include endocrine, paracrine and autocrine receptors, adrenergic receptors, lipoprotein receptors (including the low-density lipoprotein (LDL) and scavenger receptors), opiate receptors, and steroid receptors. These receptors also include surface protein receptors for asialoglycoprotein, insulin, somatostatin, somatotropins, growth factors, such as growth hormone, platelet derived growth factor, insulin-like growth factor, epidermal growth factor (EGF), $\alpha$-transforming growth factor, nerve growth factor, fibroblast growth factor, somatomedin, vasopressin, prostaglandins, eosinophil chemotactic factor, acetylcholine, thyroxine (TSH), epinephrine; endorphins, enkephalins and dynorphins; neurotensin, oxytocin, transferrin, substance P, lymphokines, such as IL-1,2,3 and -4, etc.; colony stimulating factors, such as GM-CSF-:, M-CSF, G-CSF, etc.: lipoproteins, such as LDL; and steroids, such as estrogen, androgen, glucocorticoids, corticosteroids, etc. Additional receptors include those receptors employed in the receptor-mediated endocytosis of certain microbial pathogens (e.g. viruses). Of particular interest are receptors which are either internalized or are recycled, that is, internalized into the cytoplasm and optionally returned to the plasma membrane surface. Illustrative of these receptors are the receptors for insulin, EGF, LDL, transferrin, interleukins, and asialoglycoprotein.

Modulation of the MHC Class I antigen activation may be achieved in a variety of ways. The number of MHC antigen molecules at the surface can be increased or decreased by employing compounds which activate or inhibit Class I antigen production. These compounds include interferon, dimethyl sulfoxide (DMSO), tetradecylphorbyl acetate (TPA), and retinoic acids. Instead of altering the MHC Class I antigen population at the surface, the effective concentration of Class I antigen for interacting with receptors may be reduced. It is noted that viral infections deplete Class I antigens at the surface and in appropriate situations may be used for this purpose.

Alternatively, one may modulate the interaction between MHC Class I antigen and surface receptors by employing antibodies to the MHC Class I antigen $\alpha_1$- or $\alpha_2$-domain, particularly the $\alpha_1$-domain, which may affect the ability of MHC to modulate surface expression of a receptor. Either polyclonal or monoclonal antibodies may be employed, particularly monoclonal. Alternatively, one may employ the monoclonal antibodies specific for the $\alpha_1$-domain to be used as immunogens for the production of anti-idiotype antibodies, which will mimic the confirmation of the Class I antigen epitope to which the monoclonal antibody binds. Thus, the anti-idiotype antibody may act as a substitute Class I antigen and may serve to block immune responses which are directed against self-antigens of the host, as in autoimmune diseases. The whole antibodies need not be employed, the variable region sufficing, or larger fragments such as Fab or F(ab')$_2$, Fab', etc.

The antibodies may be prepared in accordance with conventional techniques. Particularly, the Class I antigen may be used as an immunogen and injected into an appropriate host, conveniently a mouse, for initiating an immune response. One or more booster injections may be employed at intervals of two or more weeks. Two to three days after the last injection, the animal host may be sacrificed, the spleen isolated, and the B-lymphocytes immortalized. Various techniques exist for immortalization, conveniently fusion with a myeloid cell, followed by selecting for hybridomas and screening under limiting dilution conditions for hybridomas producing antibodies having the desired characteristics. Thus, in the present situation the Class I, antigen or, in the case of the anti-idiotype, the antibody with binding specificity to the domain of interest could be used in a competition assay for screening.

Instead of employing antibodies, oligopeptides may be employed which are capable of altering, either directly or indirectly, the interaction between MHC antigens and surface receptors. Altering of MHC-surface receptor interaction may be achieved by, for example, binding to the $\alpha$-helix of MHC Class I antigen. Such binding may occur through a substantially self-self interaction between the $\alpha$-helix of the native MHC antigen and a peptide having substantially the same amino acid sequence as the native MHC $\alpha$-helix. By modifying the peptide sequence, for example by substitutions, deletions or insertions, where usually from 1 to 3, usually from 1 to 2, amino acids are involved, the activity of the peptide may be vaned (i.e. enhanced).

"Non-conservative substitutions" is intended to include those substitutions which substantially differ as to polarity and/or size In Table 1 each line indicates substitutions considered to be conservative substitutions.

TABLE 1

|  | Neutral Aliphatic |
|---|---|
| Non-polar | |
| small | G, A (P) |
| large | V, I, L |
| Polar | |
| Oxy or Thio | S, T, C, M |
| Amide | N, Q |
| Aromatic | F, W, H, Y |
| Charged | |
| Acidic | D, E |
| Basic | K, R |

( )intends that the amino acid will normally not be used as a substitute for other amino acids on the same line.

While not wishing to be bound to the theory, it appears that the peptides are involved with inhibiting internalization of receptors by blocking interaction of MHC Class I molecules with receptors. In this manner, the lifetime of the ligand-receptor complex on the cell surface is extended, so thin one observes an enhanced activity as a result of binding of the ligand to the receptor. In addition, there may be other effects of the peptide, such as allosteric effects, which may enhance binding affinity of the ligand and provide activation effects (where the peptide results in activation of the receptor), so as to provide for transduction of a signal into the cytoplasm, or other effects, where the sum total of the result is an enhanced effect as compared to the absence of the peptide.

In a variety of disease states, the disease results from reduced presence of a particular receptor at the surface or reduced affinity of the receptor for the ligand. In this situation, one could reduce the density of the Class I MHC antigen or provide peptide at an appropriate concentration, so as to facilitate an increase in the amount of receptor presented on the cell surface and thus cause an increase in the probability of receptor activation and the concomitant receptor response. Conditions such as diabetes, Graves disease, arthritis, ankylosing spondylitis, Reiter's disease, analgesia, viral disease, etc., may be treated where the disease is associated with inadequate receptor response.

Alternatively in other situations, where one wishes to diminish the receptor response, one might wish to down regulate receptor binding of ligand. Illustrative of such conditions are neoplasia, arthritis, lupus erythematosus, etc., where it is desirable to reduce the response to growth factors or other secreted factors which encourage proliferation or other undesirable response. In this situation, one may treat the target cells with a drug which would enhance the population of Class I antigens at the surface.

The subject peptides may affect one activity of the receptor differently from a different activity. For example in the case of the insulin receptor, peptides mediate an increase in glucose uptake in whole cells and while the same peptides also diminish the tyrosine kinase activity of purified receptor. Thus, the subject peptides may selectively modify a receptor having a plurality of activities.

As already indicated, Class I antigen depletion may also be achieved using antibodies or oligopeptides which either bind to the Class I antigen, thereby inhibiting interaction with the receptor, or bind to the receptor, thereby inhibiting interaction with the Class I antigen. These compounds can be prepared by employing sequences comparable to polymorphic sequences, particularly in the $\alpha_1$-domain of the Class I antigen. Of particular interest are oligopeptides comprising at least a portion of one of the following sequences, where the oligopeptides comprise as the active sequence, at least six amino acids, usually at least eight amino acids, more usually at least about 11 amino acids, and fewer than 40 amino acids, more usually fewer than 30 amino acids, preferably, not more than about 25 amino acids, preferably being from about 8 to 25 amino acids, more preferably about 8 to 24 amino acids. It is understood that up to five, more usually up to about three substitutions or deletions may be made in the subject sequences, where the change will not be more than about 20 number %, usually not more than about 10 number % of the number of amino acids in the active sequence. Also the following sequences may be joined together either contiguously or by bridges of not more than about 20 amino acids, more usually not more than about 10 amino acids. Furthermore, where the sequences overlap, it is intended that the overlapping sequences not be repeated, but rather that the non-overlapping sequences be joined in proper sequence.

The oligopeptide will have at least six amino acids which are the same, or substantially the same as, a sequence included in the following sequence.

$$W\ aa^{52}\ E\ Q\ aa^{55}\ aa^{56}\ G\ P\ E\ Y\ W\ (SEQ\ ID\ NO:01) \quad 1$$

$$W\ aa^{61}\ aa^{62}\ aa^{63}\ T\ aa^{65}\ aa^{66}\ aa^{67}\ K\ aa^{69}\ aa^{70}\ aa^{71}\ Q\ (SEQ\ ID\ NO:02) \quad 2$$

$$W\ aa^{61}\ aa^{62}\ aa^{63}\ aa^{64}\ aa^{65}\ aa^{66}\ aa^{67}\ K\ aa^{69}\ aa^{70}\ aa^{71}\ aa^{72}\ aa^{73}\ aa^{74}\ aa^{75}\ aa^{76}\ aa^{77}\ aa^{78}\ aa^{79}\ aa^{80}\ aa^{81}\ aa^{82}\ aa^{83}\ aa^{84}\ aa^{85}\ (SEQ\ ID\ NO:03) \quad 3$$

$$G\ N\ E\ Q\ aa^{73}\ aa^{74}\ R\ V\ aa^{77}\ aa^{78}\ R\ aa^{80}\ aa^{81}\ aa^{82}\ R\ Y\ aa^{85}\ (SEQ.\ ID\ NO.04) \quad 4$$

wherein:

$aa^{52}$ is a neutral aliphatic amino acid of from 4 to 6 carbon atoms, particularly V, I, L or M, more particularly V or I;

$aa^{55}$ is any charged amino acid, particularly K, R, D, or E, more particularly K or E;

$aa^{56}$ is a charged amino acid, particularly D, E, K or R, more particularly E or K;

$aa^{61}$ is D or E:

$aa^{62}$ is K, R, G, or A, particularly R or G:

$aa^{63}$ is any aliphatic amino acid other than basic of from 4 to 6 carbon atoms, particularly D, E, I, L, V, N, or Q, more particularly E, N, or Q;

$aa^{64}$ is S, T, or M, particularly T:

$aa^{65}$ is any polar or basic amino acid of 4 to 6 carbon atoms, particularly N, Q, K or R, more particularly Q;

$aa^{66}$ is any aliphatic amino acid of from 4 to 6 carbon atoms, particularly L, I, V, K, R, N, or Q, more particularly K, I or N:

$aa^{67}$ is any neutral aliphatic or aromatic amino acid, particularly G, A, L, V, I, S, T,M,C,F,Y, N, or Q, more particularly C, S, Y, or M:

$aa^{68}$ is K or R, particularly K:

$aa^{69}$ is any aliphatic neutral amino acid other than A or any acidic amino acid, particularly D, E, G, S, T, or M, particularly G or T;

$aa^{70}$ is any aliphatic amino acid, neutral, polar, or basic (other than acidic) from 3 to 6, usually 4 to 6 carbon atoms, particularly N, Q, K, R, S, or T, more particularly N, Q, or K;

$aa^{71}$ is any aliphatic amino acid other than basic, usually from 2 to 5 carbon atoms, particularly G, A, S, T, D, or E, more particularly A, T or E:

$aa^{72}$ is N or Q, particularly Q:

$aa^{73}$ is S, T, F, Y, Fl, or W, particularly T or S;

$aa^{74}$ is F, Y, H, or W, particularly F;

$aa^{75}$ is K or R, particularly R:

$aa^{76}$ is an aliphatic amino acid other than basic of from 4 to 6 carbon atoms, particularly D, E, V, I, or L, more particularly E or V;

$aa^{77}$ is a polar aliphatic amino acid of from 3 to 6 carbon atoms particularly N, Q, S, T, D, or E, more particularly N, D or S:

$aa^{78}$ is a non-polar aliphatic amino acid of from 3 to 6 carbon atoms, particularly A, P, V, I, or L, more particularly L;

$aa^{79}$ is K or R, particularly R;

$aa^{80}$ is a neutral aliphatic amino acid, other than A, of from 3 to 6 usually 4 to 6 carbon atoms, particularly, S, T, N, Q, I, V or L, more particularly N, T, or I;

$aa^{8}$ is an aliphatic non-polar amino acid, particularly G, L, I, or V, more particularly L;

$aa^{82}$ is a non-acidic aliphatic amino acid other than A, of from 2 to 6, usually 5 to 6, carbon atoms, particularly K, R, G, L, I, or V, more particularly L;

$aa^{83}$ is a non-acidic aliphatic amino acid other than A, of from 2 to 6 carbon atoms, particularly K, R, G, L, I, or V, more particularly G or R;

$aa^{84}$ is an aromatic amino acid, particularly F, Y, H, or W, more particularly Y; and $aa^{85}$ is either an aromatic amino acid, particularly F, Y, H, or W, more particularly Y, or a non-polar aliphatic amino acid, preferably A.

Preferably, there will usually not be more than three mutations in the above sequence as substitutions, deletions, or insertions.

Of particular interest is an amino acid sequence of at least 6, usually at least 17, amino acids contained within the following sequence.

$$W\ D/E\ R\ aa^{63}T\ Q/R\ aa^{66}aa^{67}K\ aa^{69}aa^{70}aa^{71}Q\ aa^{73}F\ R\ V/E\ aa^{77}L\ R\ aa^{80}L/A\ L/R\ G/R\ Y\ aa^{85}(SEQ.\ ID\ NO.05)$$

wherein:

$aa^{63}$ is E, I, or N;

$aa^{66}$ is I, N, or K, particularly I;

$aa^{67}$ is A, C, S, M, or Y, particularly Y or C;

$aa^{69}$ is G, A, T, or P, particularly A or T:

$aa^{70}$ is Q, N, or K;

$aa^{71}$ is A, E, or T;

$aa^{73}$ is T, W or S $aa^{77}$ is N, S, or D;

$aa^{80}$ is I, N, or T, particularly T; and $aa^{85}$ is any amino acid, preferably Y or A, more preferably A;

and where when two amino acids are indicated at a particular site, either amino acid may be employed interchangeably. Up to three of the amino acids may be subject to conservative or non-conservative changes, there being from 0 to 2 deletions or insertions of from 1 to 2 amino acids.

Compositions of interest include an amino acid sequence contained within the following sequence:

$$N/Q\ S/T\ aa^{74}K/R\ aa^{76}aa^{77}aa^{78}K/R\ S/T\ I/L/T\ I/L/T\ (SEQ.\ ID\ NO:06)$$

wherein:

$aa^{74}$ is F, Y, or W, particularly F;

$aa^{76}$ is any is a non-acidic aliphatic amino acid other than A, particularly V;

$aa^{77}$ is N, S, or D;

$aa^{78}$ is any is a non-acidic aliphatic amino acid other than A, particularly L;

and where more than one amino acid is indicated at a sire, any one amino acid may be employed interchangeably with the other two.

The subject oligopeptides are further characterized by helix formation resulting in a structure capable of aggregation: positive and negative maxima in a circular dichroic spectrum with a profile similar to the peptide consisting of amino acids 69 to 85 of the $\alpha_1$-helix of the $D^k$ MHC Class I antigen; and the ability to bind to Class I MHC antigen.

The oligopeptides may be provided in a variety of ways, being joined to non-wild-type flanking regions, as fused proteins, joined by linking groups or directly covalently linked through cysteine (disulfide) or peptide linkages. The oligopeptides may be joined to a single amino acid at the N- or C-terminus or a chain of amino acids. The fused peptides may be extended to provide convenient linking sites, e.g. cysteine or lysine, to enhance stability, to bind to particular receptors, to provide for site-directed action, to provide for ease of purification, to alter the physical characteristics (e.g. solubility, charge, etc.), to stabilize the conformation, etc. The oligopeptide may be N-terminal, C-terminal or internal. The oligopeptide may be linked through a variety of bifunctional agents, such as maleimidobenzoic acid, methyldithioacetic acid, mercaptobenzoic acid, S-pyridyl dithiopropionate, etc. The oligopeptides may be linked to proteins to provide immunogens for the production of antibodies or to provide site-directed action. The oligopeptides may be linked, particularly by an intracellular cleavable linkage, to antibodies for site directed action. For conjugation techniques, see, for example, U.S. Pat. Nos. 3,817,837; 3,853,914; 3,850,752; 3,905,654; 4,156,081; 4,069,105; and 4,043,989, which are incorporated herein by reference.

The oligopeptides may also be modified by incorporation into the lumen of vesicles, e.g. liposomes, which in turn may be bound to ligands or receptors for direction to particular cells or tissue.

The oligopeptides may be employed in a variety of ways. For therapy, they may be administered topically or parenterally, e.g. by injection at a particular site, for example, subcutaneously, intraperitoneally, intravascularly, or the like or transdermally, as by electrotransport. The oligopeptides may also be administered subcutaneously as a self-aggregating gel so as to concentrate peptide at the desired site of action or to provide a depot of active peptide for slow release over an extended period. Furthermore, gels of peptides may serve as reservoirs for delivery of other, additional drugs such as insulin, EGF, growth hormones, and the like. Delivery of drugs in peptide gels would concentrate and retain the drug at a local site of action and provide for slow release of the drug over an extended period of time. Such delivery may decrease the dosage of drug required and may also decrease the number of treatments necessary to achieve a therapeutic effect. Where the gel contains active peptides which provide for increased surface expression of a receptor which binds a drug contained in the gel, gels may serve as a method to provide for a synergistic therapeutic effect of peptide and drug.

The formulations will usually involve a physiologically acceptable medium, such as deionized water, saline, aqueous ethanol, phosphate buffered saline, and the like. The manner of formulation will vary depending upon the purpose of the formulation, the particular mode employed for modulating the receptor activity, the intended treatment, and the like. The formulation may involve patches, capsules, liposomes, time delayed coatings, pills, or may be formulated in pumps for continuous administration. Because of the wide variety of modes of treatment, the varying responses, the different disease states, and the like, no useful limits may be given for the concentration of the active components. These can be determined empirically in accordance with known ways. See, for example Harrison's, Principles of Internal Medicine, 11th ed. Braunwald et al. ed, McGraw Hill Book Co., New York, 1987.

The oligopeptides derived from the α-helix of Class I MHC antigens may also find use in a drug screening assay. Such an assay may take advantage of the correlation between the ability of peptides to form micelles and gel-like aggregates and to inhibit surface receptor internalization mediated by native MHC antigens. This correlation of aggregative characteristics with biological activity may support the theory that peptides derived from an α-helix of Class I MHC actually bind to the portion of the Class I α-helix from which it was derived. This interaction is analogous to the self interaction of peptides having biological activity. Drug candidates which may be capable of inhibiting surface receptor internalization may then be identified by first screening the drug candidates for the ability to successfully disrupt peptide-peptide self interactions. Alternatively, the screening assay may involve competition of the drug candidate with peptide for association with either Class I MHC antigen, receptor, a saturable cell-surface binding site, or an accessory molecule(s) involve in surface receptor internalization. Drug candidates which affect receptor internalization may also be identified by screening drugs for the ability to either enhance or reduce the effect of peptides on the internalization of a selected surface receptor.

In one embodiment of the screening assay, a peptide derived from Class I MHC antigen and having modulatory activity or a substantially purified Class I MHC antigen is non-diffusably bound to an insoluble support having isolated sample receiving areas (e.g. a microtiter plate). The insoluble supports may be made of any composition to which peptide, Class I MHC antigen, or other protein can be bound, is readily separated from soluble material, and is otherwise compatible with the overall method of screening. The surface of such supports may be solid or porous and of tiny convenient shape. Examples of suitable insoluble supports include microtiter plates, membranes and beads. These are typically made of glass, plastic (e.g. polystyrene), polysaccharides, nylon or nitrocellulose. Microtiter plates tire especially convenient because a large number of assays can be carried out simultaneously, using small amounts of reagents and samples. The particular manner of binding of the peptide, Class I MHC antigen or other protein is not crucial so long as it is compatible with the reagents and overfill methods of the invention, maintains the activity or the peptide and is nondiffusable. Following binding peptide or Class I MHC antigen, excess unbound material is removed by washing. The sample receiving areas may then be blocked through incubation with bovine serum albumin (BSA), casein or other innocuous protein.

The drug candidate and varying concentrations of the oligopeptide are added to each of the sample receiving areas containing support-bound peptide or Class I MHC antigen. The oligopeptide added is of substantially the same amino acid sequence as the oligopeptide bound to the support and is labeled. The oligopeptides could be labeled, directly or indirectly, with a label which provides a detectable signal, e.g. radioisotope, fluorescers, enzyme, particle, chemiluminescer, etc. Positive controls for binding of active peptide and competitive binding of active peptide may include samples containing labeled active peptide alone and a mixture of labeled active peptide and unlabeled active peptide, respectively. Samples containing labeled active peptide and unlabeled inactive peptide which does not aggregate with the bound peptide may serve as a negative control for competitive binding with peptide. Preferably all control and test samples are performed in fit least triplicate to obtain statistically significant results. Incubation of all samples is for a time sufficient for the binding of the labeled active peptide to the support-bound peptide. Following incubation, all samples are washed free of non-specifically bound material and the amount of bound, labeled peptide determined. For example, where a radiolabel is employed in labeling the peptide, the samples may be counted in a scintillation counter to determine the amount of bound, labeled peptide.

In test samples containing the drug candidate, if the amount of labeled active peptide bound to the support-bound peptide or Class I MHC antigen is in the range of values of the positive control samples for competitive binding and is significantly less than binding of labeled peptide in the active peptide alone and negative control samples for competitive binding, then the drug candidate in the test sample is able to successfully competitively bind the support-bound peptide or Class I MHC antigen. Drug candidates capable of such competitive binding may mediate modulation of cell surface expression of a receptor with a peptide-like activity.

In an alternative embodiment, a labeled antibody having binding specificity for Class I MHC antigen and/or a peptide derived from is substituted for the labeled active peptide in the screening assay described above. This antibody may be a monoclonal or polyclonal antibody which competitively binds native Class I MHC antigen in the presence of peptide having modulatory activity. This antibody may also block aggregative interactions between peptides having modulatory activity by competitively binding to the peptides. The antibody may have binding specificity for the same or a different epitope than that with which biologically active peptides may bind during interaction with Class I MHC antigen or peptide aggregation. The antibody may be labeled, directly or indirectly, with a label which provides a detectable signal, e.g. radioisotope, fluorescers, enzyme, particle, chemiluminescer, etc. Following binding of the active peptide or Class I MHC antigen to the support, removal of excess peptide by washing and blocking of the sample receiving areas, test samples containing varying relative concentrations of a drug candidate and the labeled antibody are added. Positive controls for binding of the labeled antibody and competitive binding of labeled antibody and active peptide may include samples containing labeled antibody alone and a mixture of labeled antibody and unlabeled active peptide, respectively. Samples containing labeled antibody and unlabeled inactive peptide which does not aggregate with either the bound peptide or Class I MHC antigen may serve as a negative control for competitive binding with peptide. Preferably all control and test samples are performed in at least triplicate to obtain statistically significant results. As described above, incubation of all samples is for a time sufficient for the binding of the labeled active peptide to the support-bound peptide. Following incubation, all samples are washed free of non-specifically bound material and the amount of bound, labeled antibody determined. Drug candidates which successfully compete with the labeled antibody for association with the peptide bound or Class I MHC antigen to the support may mediate modulation of cell surface expression of a receptor with peptide-like activity.

In test samples containing the drug candidate, if the amount of labeled antibody bound to the support-bound peptide is in the range of values of the positive control samples for competitive binding and is significantly less than binding of labeled antibody in the antibody alone and negative control samples for competitive binding, then the drug candidate in the test sample is able to successfully competitively bind the support-bound peptide or Class I MHC antigen. Drug candidates capable of such competitive binding may mediate modulation of cell surface expression of a receptor with a peptide-like activity.

In a further embodiment, the screening assay may employ whole cells with saturable binding sites for either a biologically active peptide or for an antibody with binding specificty for Class I MHC antigen. Following the seeding of cells to an insoluble support, test samples containing varying relative concentrations of a drug candidate and either a labeled peptide having modulatory activity or a labeled antibody having binding specificty to MHC Class I antigen are added. Positive controls for binding of the labeled peptide or labeled antibody may include samples containing labeled peptide or labeled antibody alone. Positive controls for competitive binding may include samples containing unlabeled active peptide mixed with either labeled peptide or labeled antibody. Samples containing unlabeled inactive peptide (which does not aggregate with either the bound peptide or Class I MHC antigen) mixed with either labeled peptide or labeled antibody may serve as a negative control for competitive binding with whole cells. Preferably all control and test samples are performed in at least triplicate to obtain statistically significant results. Incubation of all samples is for a time sufficient for the binding of the labeled active peptide or labeled antibody to whole cells. Following incubation, all samples are washed free of non-specifically bound material and the amount of bound, labeled antibody or labeled peptide determined. Drug candidates which successfully compete with either the labeled peptide or labeld antibody for association with the saturable binding site of cells may mediate modulation of cell surface expression of a receptor with peptide-like activity.

In test samples containing the drug candidate, if the amount of labeled peptide or labeled antibody bound to the cells is in the range of values of the positive control samples for competitive binding and is significantly less than binding of labeled peptide or labeled antibody in the antibody alone and negative control samples for competitive binding, then the drug candidate in the test sample is able to successfully competitively bind the saturable binding site present on the cell surface. Drug candidates capable of such competitive binding may mediate modulation of cell surface expression of a receptor with a peptide-like activity.

Alternatively, the screening assay may examine the ability of a drug candidate to inhibit internalization of a selected receptor known to be affected by interaction with Class I MHC. For example, whole cells may be seeded on a soluble support. Test samples containing the drug candidate would then be added in varying concentrations to the cell monolayers. Positive controls may include samples having either biologically active peptide or an antibody with binding specificty for Class I MHC antigen. Negative controls (basal level) may include untreated samples, biologically inactive peptide or antibody which does not bind MHC Class I antigen. Following incubation for a time known to be sufficient for detection of an effect in positive control samples, labeled ligand which binds to the receptor of interest is added to all samples. For example, if the receptor of interest is the insulin receptor, then the labeled ligand may be $^{125}$I-insulin. The samples are incubated for a time sufficent for binding of the labeled ligand to receptors and then washed free of non-specifically bound ligand. In test samples containing the drug candidate, if the amount of labeled ligand bound to the cells is in the range of values of the positive control samples and is significantly more than binding of labeled ligand in the negative control samples, then the drug candidate in the test sample may mediate modulation of cell surface expression of a receptor with a peptide-like activity.

In a further alternative embodiment, the screening assay may examine the ability of a drug candidate to inhibit gel formation by active peptides. A solution containing an active peptide may be mixed with varying concentrations of the drug candidate of interest. A solution of active peptide alone may serve as a positive control for gel formation. A solution of differing ratios of active peptide and inactive, non-aggregative peptide may serve as a negative control for gel formation. The molar concentration of inactive peptide required to disrupt gel formation represents that level at which disruption of active peptide gel formation is non-specific (i.e. due to dilution of active peptide solution). Drug candidates which inhibit gel formation of active peptide at a molar concentration significantly lower than that associated with non-specific disruption of gel formation may then be capable of modulating surface receptor response with peptide-like activity. This embodiment of the screening assay may provide a quick, qualitative method for identifying those drug candidates which competitively bind peptide and thus interrupt peptide-peptide interactions.

The oligopeptides of this invention may be prepared in accordance with conventional techniques, such as synthesis (for example, use of a Beckman Model 990 peptide synthesizer or other commercial synthesizer), recombinant techniques, or the like. See, for example, Maniatis et al., *Molecular Cloning: A Laboratory Manual*, CSH Laboratory, Cold Spring Harbor, N.Y., 1982.

The following examples are offered by way of illustration and not by way of limitation.

EXPERIMENTAL

EXAMPLE 1

MHC Class I Regulation of Surface Expression of Insulin Receptor

Mutant line, R1E, derived from the murine thymoma line R1 by chemical mutagenesis (Parns and Seidman, Cell (1982) 29:661–669; Alien et al., *Proc. Natl. Acad. Sci. USA* (1986) 83:7447–7451) expresses, in contrast to R1, none of the parental H2$^k$ haplotype antigens of the C58 strain of origin due to the lesions induced in the $\beta_2$-microglobulin ($\beta_2$m) gene in R1E. Specific insulin binding to R1E murine thymoma cells and various R1E transfectants was determined, with the binding being performed as described in Gavin et al., *J. Biol. Chem.* (1973) 248:2202–2207 and Due et al., *Diabetologia* (1985) 28:749–755.

All cells were cultivated in RPMI-1640 with 15% fetal calf serum (FCS) and with the various additives as indicated (Allen et al., supra (1986)). Prior to insulin binding assays, the cells were seeded in RPMI-1640 with 10% FCS and at a density of $2\times10^4$ cells/ml, harvested three days later, viability was assured to be >95% by trypan blue dye exclusion, and the cells subsequently resuspended in assay buffer for insulin binding at a concentration of $7.5\times10^7$ cells/ml. $^{125}$I-labeled human insulin in a final concentration of 50 pM (labeled in the A14 position and obtained from NOVO A/S, Denmark) was added and the cells incubated for 90 min at 18° C. in a shaking water bath. Two mls ice-cold assay buffer were added at the end of incubation, the cells centrifuged at 300 g for 5 min, centrifuged at 100 g for 10 min and the amount of $^{125}$I-insulin in the pellet counted in a γ-counter. Non-specific binding was estimated as the amount of $^{125}$I-insulin binding in the presence of $10^{-6}$M unlabeled insulin, and specific insulin binding calculated as the difference in binding of $^{125}$I-insulin with and without unlabeled insulin. Specific binding <1% was estimated to be non-specific considering the Scatchard plots and the specific binding as related to cell number.

Scatchard plots were complied, with each point representing duplicate or triplicate samples, for each of lines R1, R1E, R1E/$\beta_2$m, R1E/D$^b$, R1E/$\beta_2$m/K$^b$, R1E/$\beta_2$m/D$^b$, R1E/$\beta_2$m/D$^b$δ, and R1E/$\beta_2$m/D$^b$-(1+2) with $3\times10^7$ cells per sample and. The Scatchard plots were repeated 3–10 times for each determination. Only R1 and R1E/$\beta_2$m/D$^b$ displayed applicable amounts of insulin receptor (IR). The curve observed shows that in addition to high affinity IR, these cells also have appreciable amounts of receptors with lower affinity for insulin, which may to some extent be due to the indirect effects of transfection and/or co-expression of other insulin binding receptors, such as those for insulin-like growth factor I (IGF-I) (Rechler and Hessley In *Polypeptide Hormone Receptors* (ed B. I. Posner) pp. 227–297, Marcel Dekker, New York (1985)).

R1 murine thymoma cells have a cell surface density of IR comparable to other lymphocyte cell populations in contrast to the human IM-9 cell line, an Epstein-Barr virus transformed cell line with exceptionally high amounts of non-functional IR often used for insulin assays. It was accordingly necessary in the R1/R1E system to use comparatively high amounts of cells per sample. Titration of specific insulin binding as related to cell number demonstrated that the optimal cell number per sample for specific insulin binding was $7\times10^7$ cells, an impractical number of cells to use on all Scatchard plots. The curves for R1 and R1E/$\beta_2$m/K$^b$ show that these two lines did not express significant amounts of IR.

Insulin receptor mRNA in R1, R1E and R1E transfectants was determined as follows. Total RNA was isolated from cells as per Chirgwin et al., *Biochemistry* (1979) 18:5294–5299, and poly A+ RNA selected as per Mantarts et al., *Molecular Cloning: A Laboratory Manual* CSH Laboratory, Cold Spring Harbor, N.Y., (1982). For Northern blot analysis 5 μg of poly A+ selected murine liver mRNA was fractionated on a 1.0% agarose-formaldehyde gel (Church and Gilbert, *Proc. Natl. Acad. Sci. USA* (1984) 81:1991–1995) and blotted on a Zeta-probe nylon membrane (BioRad Laboratories, Richmond, Calif.). Insulin receptor-specific sequences were detected by hybridization with a synthetic DNA oligonucleotide representing amine acids 732–741 inferred from the insulin receptor cDNA precursor (Ullrich, el al., *Nature* (1985) 313:756–761). Hybridization and washing conditions were performed as per Church and Gilbert, supra (1984), except that hybridization and washes were at 45° C. Approximately 1 μg and 1:10 dilution of poly A+ selected mRNA from mouse liver and appropriate cell lines was spotted on the Zeta-Probe membranes and hybridized as above. Molecular weight markers for Northern blot analysis were purchased from Bethesda Research Laboratories (Bethesda, Md.). A predominant species of 4.8 kb from mouse liver hybridized to the human insulin receptor oligonucleotide. This species was also noted by Ullrich et al., supra (1985), in human placental mRNA with radiolabeled cloned human insulin receptor cDNA sequences.

The surface proteins of the various cell lines were screened using fluorescent labeled monoclonal antibodies and a fluorescence-activated cell sorter (FACS). The results are summarized in Table 2.

TABLE 2

Fluorescence-Activated Cell Sorter (FACS) Analysis
R1, R1E and the Transfectants for Expression of H-2 and $\beta_2$m

| | | No. FITC-molecules/cell × $10^{-3}$ [a,b] | | | | | | |
|---|---|---|---|---|---|---|---|---|
| Cell Lines[c] | H-2 specificity monoclonal antibodies[a] | $K^kD^k$ (28-8-6) | $K^k$ (11.4) | $K^b$ (20-8-4) | $D^k$ (15-5-5) | $D^b$ (28-14-8) | $\beta_2m^b$ | $\beta_2m$ |
| R1 | | 750 | 505 | <10 | 435 | 16 | <10 | 175 |
| R1E | | 25 | <10 | <10 | <10 | <10 | <10 | <10 |
| R1E/$\beta_2$m | | 290 | 80 | 15 | 90 | 15 | 225 | 80 |
| R1E/$D^b$ | | 145 | 30 | <10 | 30 | 570 | <10 | <10 |
| R1E/$\beta_2$m/$D^b$ | | 370 | 115 | 10 | 170 | 1240 | 450 | 390 |
| R1E/$\beta_2$m/$K^b$ | | 400 | 215 | 410 | 260 | <10 | 510 | 425 |
| R1E/$\beta_2$m/$D^b$ + Ab | | 345 | 170 | 10 | 320 | 250 | 200 | 105 |
| R1E/$D^b$-(1 + 2) | | 190 | 70 | <10 | 50 | 825 | <10 | <10 |
| R1E/$\beta_2$m/$D^b$-(1 + 2) | | 350 | 105 | 10 | 130 | 880 | 210 | 160 |

Legend to Table 2

[a] The monoclonal antibodies used for screening have been described (Ozato et at., Transplantation (1982) 34:113–120). For staining, $10^6$ cells were incubated with 1 μg antibody/ml at 4° C. with fluorescein-isothiocyanate (FITC) conjugated rabbit anti-mouse polyclonal antibody (purchased from DAKO, Denmark). The cells were washed twice in PBS and analyzed. Cells incubated with FITC-conjugated secondary antibody served as negative controls. A shift of >15 channel numbers on the linear fluorescence scale was considered significant; all samples were analyzed both on a logarithmic and linear fluorescence scale. The absolute number of bound FITC molecules per cell was estimated as described (Due et al., supra, (1985)). It should be noted that comparison of FACS data to estimate the relative proportion of different H-2 molecules only is reasonable when the same primary antibody is used.

[b] Expression of H-2 was determined for all lines examined both by solid phase radioimmunoassay (RIA) with $^{125}$I-labeled protein A as secondary reagent and by FACS as described above. Briefly, RIA assays (Weiss et al., Nature (1984) 310:650–655) were done by plating 5×10$^5$ cells (96 well microtiter plate) in 50 μl diluted antibody in MEM+ 10% FCS was then added. The cells were incubated 4 hr at 4° C., pelleted and washed with MEM+10% FCS. $^{125}$I-Protein A was added (Amersham) to 100,000 cpm and incubated for 16 hr at 4° C. Cells were pelleted and washed three times with MEM+10% FCS before counting in a Beckman Gamma Counter. All samples were done in duplicate and with less than 5% variation on all samples counted.

[c] The R1, R1E lines, the H-2K and H-2D genes, and the procedures for transfection have been described in detail previously (Allen et al Proc. Natl. Acad. Sci. USA (1986) 83:7447–7451; Goodenow et al., Science (1982) 215:677–679). The various designations indicate: R 1E/$\beta_2$m, R1E transfected with $\beta_2$m, R1E/$D^b$; transfected with $D^b$; R1E/$\beta_2$m/$D^b$, R1/$\beta_2$m/$k^b$ transfected with $\beta_2$m and $K^b$; R1E/$\beta_2$m/$D^b$+α-$D^b$.R1E transfected with $\beta_2$m and $D^b$, but with the $D^b$ cell surface antigen down-regulated due to the presence of a monoclonal antibody to $D^b$; R1E/$\beta_2$m/$D^b$-(1+ 2), transfected with $\beta_2$m and truncated $D^b$ gene, expressing only the α3-domain on the cell surface: R1E/$\beta_2$m/$D^b$-(1+2), transfected with truncated $D^b$, expressing only the α3-domain.

EXAMPLE 2

Study of MHC Class I Peptide Regulation of Purified Insulin Receptor

Peptides.

The two MHC Class I derived peptides $D^k$-(61-85), and $K^k$-(61-85) are both from the same region of the α$_1$ domain of the MHC Class I molecules (Klein, Natural History of the Major Histocompatibility Complex (Wiley, N.Y.)). Both peptides were synthesized by Applied Biosystems, Inc., (Foster City, Calif.), and quality controlled by mass spectrometry.

The $D^k$-(61-85), and $K^k$-(61-85) peptides were iodinated for some experiments using carrier-free Na$^{125}$I (Amersham) and iodobeads (Pierce) by incubating for 20 min, then purified by reversed-phase HPLC on a C$_{18}$ column (Beckman) in a linear 30–50% gradient of CH$_3$CN in 5 mM trifluoroacetic acid (TFA). The $^{125}$I-labeled peptide eluting first was stored at 4° C. in 50% CH$_3$CN/5 mM TFA. The labeled peptides were stable under these conditions for at least 3 months.

Control Peptides: ACTH-(1-24) (human), ACCK-33 (porcine), dynorphin A (porcine), β-endorphin-(1-27) (camel), glucagon (human), and prosomatostin-(1-32) (porcine) were all purchased from Peninsula Laboratories, Belmont, Calif. The A-chain and B-chain of insulin (porcine) and glucagon-(1-21) (human) were obtained from Novo Industry, Denmark. ACTH-(1-24) was used a routine control peptide.

Purified Insulin Receptor (IR).

The purified human IR and the cloned cytoplasmic kinase domain (IRKD) have been described (Ellis el al., (1988) Virology 62: 1634–39; Roth et al., (1986) J. Biol. Chem. 261:3753–57). Briefly, the human IR was purified from placenta by immunoaffinity columns, using monoclonal antibodies and binding of IR to wheat germ agglutinin. The product was a tetramer with two heavy chains, each≈130 kDa, and two light chains, each≈90 kDa.

Tyrosine Kinase Activity.

The cytoplasmic, cloned IRKD was constructed from the IR sequence (Ebena et al., (1985) Cell 40:747–758; Ullrich et al., (1985) Nature 313:756–761) and expressed in insect cells by using a baculovirus expression vector. The domain is soluble (M$_r$≈48 kDa) and the kinase activity is constitutively expressed in vitro. The IRKD was purified to homogeneity by immunoaffinity chromatography.

The procedures to measure kinase activity of the purified IR and IRKD, as well as the effects of insulin, have been described elsewhere (Roth et al., (1986) supra). Briefly 5.0 µl purified IR was mixed with 5.0 µl insulin (final concentration 1.0 µM) and the buffer (50 HEPES, pH 7.6, 150 mM NaCl, 0.1% Triton X-100) added to a final volume of 20 µl. When peptide was used, it was added in 5.0 µl, the volume adjusted to 20 µl by adding buffer, and the mixture incubated (1 hr, 4° C.). After incubation, 10 µl of a solution containing 2.5 µCi $^{32}$P-labeled ATP (3,000 Ci/mmol: γ-labeled; Amersham) 50 mM HEPES, pH 7.6, 150 mM NaCl, 0.1% Triton X-100, 37.5 µM unlabeled ATP, 15 mM MgCl$_2$, and 6 mm MnCl$_2$ was added to a final volume of 30 µl. The mixture was then incubated for 30 min at 24° C.

After incubation, 15 µl sample buffer was added, the sample boiled for 5 min and then run on 10% SDS-PAGE overnight. The gel was dried, and autoradiograms processed with an exposure time of 5 to 10 hr. For quantitative estimates the β-subunit band of the IR and the IRKD bands were excised and counted dry (Cerenkov) in a scintillation counter.

Substrate phosphorylation was done with poly-([Glu,Tyr];4:1) (Sigma) as substrate. The substrate was added to a final concentration of 1.0 mg/ml and the phosphorylation assay was conducted as described above. Quantitative estimates were determined by excising the entire lane from just below the insulin receptor band to the 20-kD marker and quantitating the amount of associated radioactivity by either placing the sample in a scintillation counter or precipitating the sample with TCA and determining the amount of TCA precipitate-associated radioactivity. For the latter, a 5 µl sample was dotted on to 3 MM paper (Whatman), washed 30 min in ice cold 10% TCA, boiled 10 min in 5% TCA, washed twice in distilled water, washed twice in ethanol, dried and counted.

Insulin Binding.

Porcine monoiodinated [$^{125}$I-insulin (iodinated at Tyr A 14; 1,900–2,000 Ci/mmol) was obtained from NOVO Industry and Amersham. Unlabeled porcine insulin (NOVO) was dissolved in 10 mM HCl at 1 mM and stored immediately at −20° C.

The plate assay for insulin binding to its purified receptor has been described (Morgan and Roth (1985) Endocrinology 116, 1224–1226). Briefly, 50 µl of affinity-purified rabbit anti-mouse IgG (Jackson Immuno Research Lab., Inc., West Grove, Pa.) (40 µg/ml) in 20 mM NaHCO$_3$, pH 9.6, was added to 96-well polyvinyl chloride (PVC) plates. The plates were incubated (17–20 hr, 4° C.), washed thrice in 50 mM HEPES, pH 7.8, with 150 mM NaCl, 0.1% Triton X-100, 0.05% BSA, and 2×10$^{-8}$M monoclonal antibody (Amac, Inc., Westbrook, ME) was added. After incubation (1 hr, 24° C.), the plates were washed and insulin binding measured.

For binding measurements, $^{125}$I-insulin (3×10$^{-10}$M) was added together with increasing amounts of unlabeled insulin, and incubated (90 min, 24° C.), washed, and the amount of free and bound $^{125}$I-labeled insulin measured. Bound insulin was determined by eluting IR off the plate with 0.1M HCI and measuring the amount of IR eluted in a γ-counter. For data analysis, non-specific binding was defined as the amount bound in presence of 10$^6$M unlabeled insulin.

RESULTS

The effect of D$^k$-(61-85) on both substrate (poly-[E,Y]) phosphorylation and IR autophosphorylation as a function of the peptide concentration, wherein IR tyrosine kinase activity is induced with 10$^{-6}$M insulin, was determined. Both IR phosphorylation and autophosphorylation were strongly inhibited at a concentration of 10 µM D$^k$-(61-85). The basal activity of IR (no insulin added) wits inhibited 24–40% by D$^k$-(61-85) and K$^k$-(61-85). The effect of K$^k$-(61-85) was significantly weaker than D$^k$-(61-85) on autophosphorylation, with EC$_{50}$ values [95% confidence intervals] of 4.0 µM [2.2–7.2 µM] and 1.2 µM [0.3–2.2 µM] for K$^k$(61-85) and D$^k$-d(61-85), respectively, whereas no difference was observed with respect to substrate phosphorylation. None of the control peptides (e.g. ACTH-(1-24) are substrates for IR tyrosine kinase.

No significant depletion (degradation or adsorption), its examined by HPLC and $^{125}$I-labeled D$^k$-(61-85), K$^k$-(61-85), ACTH-(1-24), or dynorphin A was observed during the experimental period at concentrations above 0.1 µM. The D$^k$-(61-85) peptide does not affect IRKD phosphorylation, as demonstrated by pre-incubation of maximally autophosphorylated and $^{32}$P-labeled IR for 1 hr on ice with 10 µM peptide and subsequent incubation with 500 µM cold ATP for 0–60 min at room temperature.

The D$^k$-(61-85) had no effect on the binding of insulin to IR. The EC$_{50}$ IR autophosphorylation was about 3×10$^{-9}$M insulin, corresponding approximately to K$_d$(2.8×10-9M). D$^k$-(61-85) at a concentration of 10 µM inhibits autophosphorylation at all insulin concentrations.

D$^k$-(61-85) at a concentration of 3 µM inhibits the insulin-induced IR autophosphorylation, but not the insulin receptor kinase domain phosphorylation, when IR and IRKD are used at comparable activities. IR is not a significant substrate for IRKD in the absence of insulin. IR becomes a significant substrate for IRKD when insulin is added. This observation is facilitated by the inhibitory effect of the peptide on IR autophosphorylation, because the IR phosphorylation as mediated by the tyrosine kinase of IR itself and the phosphorylation mediated by IRKD would otherwise be indistinguishable.

In the next study, the uptake of glucose in rat adipocytes was performed. Adipocytes were prepared from non-starved male rat epididymal fat pads (1.2–1.6 g fat per rat) by collagenase digestion. The digest was filtered (25 µl), washed and resuspended in approximately 4 times the cell volume (estimated by lipocrit) in Krebs-Ringer's/HEPES (KRH) with 5% BSA. Only plastic tubes were used. An aliquot was removed for Coulter counting after staining with 2% osmium tetroxide, filtration and dilution in saline. 50 µl of adipocyte suspension was added to the pre-incubation mix; 300 µl buffer, 50 µl insulin (80 nM) or buffer: 50 µl test solution (10×) or buffer and incubated for 30 min at 37° C. in a shaking water bath. A blank without cells was included for background counting. D-[$^{14}$C]-glucose was subsequently added (about 10$^5$ dpm/sample) and incubation continued for 60 min. The incubation was terminated by layering the 400 µl sample on top of silicone oil, followed by a 30 sec. microcentrifuge spin, and cutting the adipocytes (thin layer of cells on top of the oil, buffer trader oil) into LS vials with scintillation fluid. Glucose concentration was about 300 nM (specific activity=295 mCi/mmol).

The effect of increasing concentrations of insulin in 30 µM D$^k$-(61-85) on glucose uptake was determined. Insulin induced maximally an 8–11 fold increase in glucose uptake as compared to basal uptake. Addition of D$^k$-(61-85) increased the maximal uptake to about 14–18 fold of basal, a glucose uptake above maximal insulin stimulation. At low concentrations of insulin (plasma level and lower), 30 µM D$^k$-(61-85) increased glucose uptake is equal to or more than that induced by insulin on a molar basis.

Various fragments of $D^k$-(61-85) were prepared by enzymatic digestion with specific peptidases: endo K, which gave fragments 60-68 and 65-85; endo E, which gave fragment 78-85; CP Y, which provided fragment 61-84; and in addition, the starting fragment was iodinated, which would be expected to occur at the terminal tyrosines. Each of the fragments were tested for biological activity after purification (greater than 95%) by HPLC and added to the cells to achieve a final concentration of 30 µM. The results reported as percent activity of the mean ± standard error, with the starting fragment being 100 are as (61-68) 19±22; (69-85) 87±2; (78-85) 15±3; (61-84) 19±3; iodinated fragment 9±10.

The effect of $D^k$-(61-85) in whole rats was determined. $D^k$-(61-85) (2.5 mg/kg) and insulin (10 µg/kg) on the blood glucose levels in rats (100–300 g) was determined. The peptide and insulin were injected intravenously after the animals had been anesthetized with pentobarbital. All animals were starved 16–20 hr prior to experimentation. Each determination was based on results as obtained from 42 rats, where the same rats were used in the four treatment schedules: control, peptide alone, insulin alone, and insulin plus peptide. The control showed no significant change in blood glucose over the 240 min during which determinations were made. At about 20 min after injection of peptide, the blood glucose had dropped to about 65% of its original value and then slowly rose back to about the original value at about 90 min and was maintained about the same level. A similar result was observed with the injection of insulin. However, where the insulin and peptide were injected together, the glucose dropped within about 20 min to about 55% of its original value, slowly rose to about 85% of its original value at about 195 min, and then gradually increased to about 90% at about 240 min. Calculation of the area between the control curve and the experimental curves from T=0 to T=240 min showed that the area for insulin plus peptide is significantly larger than that of either insulin or peptide alone, indicating a prolonged hypoglycemic period as compared to the injection of insulin or peptide alone. These results support that not only does the peptide have an effect on the insulin receptor in vivo, but also that skeletal muscle, the main organ responsible for glucose transport, is affected.

Based on the above data, it may be concluded that $D^k$-(61-85) peptide enhances cellular glucose uptake both in the absence and presence of insulin. The peptide effect is increased upon stimulation with insulin. Maximal peptide effect is reached at a peptide concentration of 10–20 gM. The peptide causes enhanced glucose uptake significantly above that induced by maximal insulin stimulation. The effect in vitro is maximal after 20 min incubation of the cells with peptide. Intravenous injection of 2.5 mg/kg $D^k$-(61-85) peptide causes a decrease in blood glucose in whole animals. It is accentuated when insulin is injected together with the peptide. In these experiments the levels of serum-insulin were unchanged.

EXAMPLE 3

Class I MHC Peptide Regulation of EGF Receptor

Peptides.

Peptides (Table 3) were synthesized by Applied Biosystems, Inc. (Foster City, Calif.). The crude $D^k$-(61-85) peptide was purified by preparative high performance liquid chromatography (HPLC) to better than 97% homogeneity as judged by analytical HPLC monitoring of absorbance at 214 and 278 nm. The $\alpha_2$- and $\alpha_3$-derived peptides were more than 90% pure.. Identity was confirmed by amino acid composition and mass spectrometry. The peptides were dissolved in 0.1M HCl and stored at 1.0 mM in 200 µl aliquots at −80° C.

TABLE 3

| Peptide | Sequence |
| --- | --- |
| $D^k$-(61–85) | ERETQIAKGNEQSFRVDLRTLLRYY (SEQ ID NO: 07) |
| $D^b$-(137–161) | DMAAQITRRKWEQSGAAEHYKAYLE (SEQ ID NO: 08) |
| $D^b$-(152–176) | AAEHYKAYLEGECVEWLHRYLKNGN (SEQ ID NO: 09) |
| $D^b$-(197–221) | GEVTLRCWALGFYPADITLTWQLNG (SEQ ID NO: 10) |

MHC Class I Derived Peptides

Hormones.

EGF (mouse) and PDGF (human) were purchased from Collaborative Research, Inc., Bedford, Mass. $TGF_\alpha$ (rat) was purchased from Peninsula Laboratories, Belmont, Calif. $^{125}$I-labeled EGF (480 Ci/mmol) was purchased from ICN Biomedicals, Inc.

Preparation of Adipocytes.

The procedure has been described in detail previously. Briefly, male Wistar rats (100–150 g) were decapitated, and the epididymal fat pads removed and minced with scissors into KRHB (Krebs-Ringer/HEPES/Bovine serum albumin (BSA) buffer: 80 mM NaCl, 4.7 mM KCl, 2.5 mM $CaCl_2$, 1.2 mM $MgSO_4$, 50 mM HEPES, 5% BSA (Sigma, radioimmunoassay grade), pH 7.2) containing 5 mM D-glucose and 1 mg/ml collagenase (type I, Worthington) and digested (1 hr, 37° C.) with gentle shaking (250 cycles per minute). The adipocytes were washed five times in KRHB (each wash in a volume ten times the cell volume). The adipocyte layer was finally diluted with KRHB to a 10% (v/v) suspension as estimated by the volume of packed cells (lipocrit).

Glucose uptake in vitro.

The uptake of [$^{14}$C]glucose (D-IU-$^{14}$C]glucose, Amersham, (300 Ci/mol)) by isolated rat adipocytes wits measured as follows unless otherwise stated: 50 µl adipocyte cell suspension was pipetted into "Nunc-Immuno tube minisorp" (Nunc, Denmark) and preincubated at 37° C. with gentle shaking (225 cycles per minute) for 30 min. Hormones and peptides were added in 50 µl KRHB and incubated for 30 min at 37° C. Before addition to cells, all solutions were neutralized to pH 7.2. [$^{14}$C]glucose tracer (≈100,000 dpm) was added and the incubation continued for another 20 min at 37° C. The assay was terminated by centrifugation of 100 µl sample on top of 250 µl silicone oil (Thomas Scientific) 500 µl tubes in a microcentrifuge (10, 000× g) for 1 min. The tube was cut just below the adipocyte layer and the amount of radioactivity in the adipocytes determined by scintillation counting. The precise concentration of [$^{14}$C]glucose was calculated from total counts added. Data were not corrected for trapping, which in previous experiments was found to be negligible.

Cell-associated $^{125}$I-labeled EGF.

50 µl adipocyte cell suspension was pipetted into "Nunc-Immuno tube minisorp" (Nunc, Denmark) and preincubated at 37° C. with gentle shaking (225 cycles per minute) for 30 min. The cells were incubated for 30 min at 37° C. with 50 µl KRHB containing 600 pM $^{125}$I-labeled EGF and different concentrations of non-radioactive EGF. The assay was terminated by centrifugation of 75 μl sample as described above for glucose uptake, and the cell-associated as well as the free $^{125}$I-labeled EGF was determined with a δ-counter. Non-specific cell-associated $^{125}$I-labeled EGF was defined as cell-associated $^{125}$I-labeled EGF in the presence of 128 nM non-radioactive EGF. The data were calculated as specific cell-associated $^{125}$I-labeled EGF and the maximal value was in each experiment set to 100%.

RESULTS

EGF alone stimulated glucose uptake in rat adipocytes ≈50% above the basal level. However, when $D^k$-(61-85) peptide was added at a concentration of 30 μM, the glucose uptake was enhanced 5–6 fold above the basal uptake level. The peptide did not affect the $EC_{50}$ for the EGF effect on glucose uptake. Maximal effect of EGF and $D^k$-(61-85) was obtained after approximately 10–20 min. The peptide was active in a concentration range of 5–30 μM and had an $EC_{50}$≈10–15 μM. The maximal effect obtained with EGF and peptide alone was ≈50% of the maximal effect obtained with insulin. EGF and peptide, in combination with increasing concentrations of insulin, resulted in increasing glucose uptake until the maximal level attained with insulin and peptide was reached.

Experiments with $^{125}$I-labeled EGF demonstrated specific cell-associated EGF with an apparent affinity in the low nanomolar range, which corresponds to the affinity for EGF binding reported with adipocytes and other cell types. The presence of the peptide did not affect the binding affinity of $^{125}$I-labeled EGF. The total cell-associated $^{125}$I-labeled EGF was unaffected by the presence of peptide 119±12 (mean±S.E.M.; no peptide=100; n=3). Peptide also did not affect the amount of non-specific cell-associated $^{125}$I-labeled EGB (57±8 with peptide versus 53±12 without peptide).

Incubation of adipocytes with 50 nM $TGF_\alpha$ increased [$^{14}$C]glucose uptake ≈50% above basal, whereas 50 nM $TGF_\alpha$ in combination with 30 μM $D^k$-(61-85) increased [$^{14}$C]glucose uptake ≈5 fold above basal. This effect of $TGF_\alpha$ alone or in combination with $D^k$-(61-85) on [$^{14}$C] glucose uptake is thus similar to the effect found for EGF.

Platelet derived growth factor (PDGF) alone or together with $D^k$-(61-85) had no effect on glucose uptake in adipocytes.

Three other peptides derived from the MHC class I molecule were also tested for their effect on glucose uptake when combined with EGF. $D^b$-(137-161) and Db-(152-176), derived from the 60 $_2$ region, and $D^b$-(197-221), derived from the $\alpha_3$ region, had no or only a small effect on glucose uptake compared to the $D^k$-(61-85) peptide.

EXAMPLE 4

Amino Acid Residues of MHC Class I Peptide Essential for Biological Activity

Materials and Methods

Glucose Transport in Adipose Cells.

The biological activity of the peptides was measured by their effect on glucose uptake in rat adipose cells as described (Stagsted, et al. (1991) *Biol. Chem.* 266:12844–12847). Briefly, rat adipose cells were obtained from epididymal fat pads and suspended in Krebs-Ringer HEPES buffer (KRH) with 5% bovine serum albumin at a lipocrit of 10% (final). The peptide effect was measured in cells maximally stimulated with insulin (8 nM). After equilibration at 37° C. for 30 min the cells were incubated for 30 min at 37° C. with buffer (basal), 8 nM insulin plus peptide. $^{14}$C-D-glucose was added, and the cells were incubated for an additional 30 min and harvested on oil. Biological activity was measured by a dose-response curve to interpolate the $EC_{50}$ value, taking the maximum enhancement of insulin effect (about 40% over the insulin-only maximum) as 100%. Most of the peptides were not tested at higher concentrations than 30 μM. Peptides that enhanced the maximum insulin effect by less than 20% at 30 μM were considered inactive. Accordingly, three categories of peptides were defined: Full activity, $EC_{50}$<10 pM; reduced activity, 10 μM≤$EC_{50}$≤30 μM; no activity, $EC_{50}$>30 μM.

Peptides.

The peptides were assembled stepwise either on a phenylacetamidomethyl (PAM) resin using the t-Boc NMP/HOBt protocol of an Applied Biosystems Model 430A peptide synthesizer, or on a p-alkoxy benzyl alcohol (Wang) resin using a modified Fmoc/BOP protocol of a Milligen/Biosearch Model 9600 synthesizer. The side chain protecting groups were as follows: for t-Box chemistry, Arg(MTS), Asp(OChx), Glu(OBzl), Lys(Cl—Z), Ser(Bzl), Thr(Bzl), and Tyr(Br—Z); for Fmoc chemistry, Arg(Pmc), Asp(OtBu), Glu(OtBu), Lys(t-Boc), Ser(tBu), Thr(tBu) and Tyr(tBu). The t-Boc-assembled peptides were deprotected/cleaved from the solid support using HF in the presence of anisole, ethanedithiol, and dimethylsulfide as scavengers. After conversion of the hydrofluoride to the acetate salt by ion-exchange column chromatography, the peptides were purified to greater than 98% homogeneity by preparative HPLC rising a Vydac C18 (2.2×25 cm) column and appropriate linear gradients of 0.1% TFA-buffered acetonitrile in 0.1% aqueous TFA. The Fmoc-assembled peptides were deprotected/cleaved from the resin using TFA in the presence of thioanisole, ethanedithiol, water and phenol as scavengers, and purified by preparative high performance liquid chromatography as described above. The desired peptides were confirmed by sequence analysis, amino acid composition, and fast atom bombardment mass spectrometry. The peptides were activated by incubation of 1 mM stock solution at 37° C. in 0.1M NaCl overnight (Stagsted, et al. (1991) *J. Biol. Chem.* 266:12844–12847).

Circular Dichroism (CD).

CD spectra were recorded on a JASCO J-600 calibrated against d-camphorsulfonic acid using ΔE (290.5 nm)=+2.38$M^{-1}$ $cm^{-1}$. Rectangular cuvettes with path lengths of 0.01 cm were used for recording spectra of 1 mM peptide stock solutions.

Aggregation.

Peptide stock solution was diluted in KRH buffer to 30 μM, incubated (30 min, 37° C.), then centrifuged at 12,000 g for 10 min. The amount of peptide remaining in solution was measured spectrophotometrically by absorbance at 278 nm (E 1200 $M^{-1}$ $cm^{-1}$ per tyrosine residue).

RESULTS

Biological Activity.

The $D^k$-(62–85) and $D^k$-(65-85) peptides were analyzed by alanine scan (Cunningham and Wells (1989) *Science* 244: 1081–1085; Cunningham and Wells (1991) *Proc Natl Acad Sci (USA)* 88:3407–3411; Wells (1991) *Methods Enzymology* 202:390–411) which involves systematic replacement of residues with alanine to assess the importance of each residue for biological activity. Table 4 presents the potency of $D^k$-(62-85) and $D^k$-(65-85), of 13 peptides in the alanine scan, and of five additional peptides of interest. FIG. 1 summarizes the relative importance of each residue in the peptide with respect to biological activity and ordered structure as well as the position of the residues on the α-helix. Substitution of Phe$^{74}$ (d), Leu$^{81}$ (f), and Leu$^{82}$ (g), all resulted in loss of activity. Substitution of Ala for Phe$^{74}$ produced a peptide which was completely inactive even at 90 μm, the highest concentration tested. Peptides with alanine instead of Leu$^{78}$ (e), Arg$^{83}$ (h), or Tyr$^{84}$ (i) all had reduced activity compared to D$^k$-(65-85) (b). Replacement of Glu$^{71}$ (c) or Tyr$^{85}$ (j) yielded peptides that were even more potent than the original.

The alanine scan with double residue changes showed (in m) that neither Asn$^{70}$ nor Asp$^{77}$ are important for activity. Peptide 1 had reduced activity, but the data did not allow for a determination as to whether Gly$^{69}$ or Val$^{76}$ is most important. The three other peptides with double alanine substitutions (k, n, o) were all inactive. In peptide k the essential residue is likely to have been Arg$^{75}$, as residues 62–68 can be deleted entirely (cf. a,b) without loss of activity. The data did not allow for a determination as to whether the inactivity of peptides n and o were due to substitution of only one or both of the residues. However, as the chimeric peptide r, with Gly$^{79}$, was moderately active, Gln$^{72}$ seems more responsible than Arg$^{79}$ for the loss of activity in peptide n.

giving less than 20% enhancement at 30 μM were considered inactive (EC$_{50}$>30 μM).

The essential role of Phe$^{74}$ is shown not only by the inactivity of d, as well as p and q (which contain many of the other residues shown to be essential), but most dramatically by the fact that the inactive human peptide s became fully active on changing Asp$^{74}$ to Phe$^{74}$ in peptide t.

Circular Dichroism (CD).

Residues identified in the alanine scan to be important for biological activity were examined for their role in the maintenance of an ordered structure. Measurements at 1 mM in 0.1M NaCl yielded a variety of complex CD spectra, so that simple classification into recognized structures (such as a-helix; 9, 10) was often not possible. Peptide j, which is fully active, hits a spectrum with maxima at 205 nm (negative) and 195 nm (positive), suggesting a high content of ordered structure. The original unsubstituted peptides a and b as well as the two other most active peptides (c, t) have a similar positive CD signal at 195 nm. Peptides h and k, with reduced activity and no activity, respectively, have CD spectra with both a positive and negative maximum, but without the typical profile of peptide j. Peptides (e, i, r), all of which have reduced activity, and the inactive peptides (f, n, o, s) also fall into this category. The CD spectrum of

TABLE 4

Sequence, Biological Activity, and Aggregation of MHC Class I-Derived Peptides.

| PEPTIDE | SEQ ID NO: | SEQUENCE 62 65 70 75 80 85 | REDIDUE(S) SUBSTITUTED | EC$_{50}$$^a$ (μM) | Aggregation$^b$ |
|---|---|---|---|---|---|
| D$^k$-(62–85) | 11 | RETQIAKGNEQSFRVDLRTLLRYY | | 2 | 70 ± 2 |
| D$^k$-(69–85) | 12 | GNEQSFRVDLRTLLRYY | | 5 | NT$^c$ |
| SINGLE SUBSTITUTIONS: | | | | | |
| [Ala$^{71}$]-D$^k$-(69–85) | 13 | GNAQSFRVDLRTLLRYY | E | 3 | 50 ± 10 |
| [Ala$^{74}$]-D$^k$-(62–85) | 14 | RETQIAKGNEQSARVDLRTLLRYY | F | >90 | 33 ± 4 |
| [Ala$^{78}$]-D$^k$-(69–85) | 15 | GNEQSFRVDARTLLRYY | L | 2 | 39 ± 6 |
| [Ala$^{81}$]-D$^k$-(69–85) | 16 | GNEQSFRVDLRTALRYY | L | ≈3 | 64 ± 6 |
| [Ala$^{82}$]-D$^k$-(69–85) | 17 | GNEQSFRVDLRTLARYY | L | ≈50 | 35 ± 4 |
| [Ala$^{83}$]-D$^k$-(69–85) | 18 | GNEQSFRVDLRTLLAYY | R | ≈20 | 91 ± 1 |
| [Ala$^{84}$]-D$^k$-(69–85) | 19 | GNEQSFRVDLRTLLRAY | Y | ≈15 | 89 ± 2 |
| [Ala$^{85}$]-D$^k$-(69–85) | 20 | GNEQSFRVDLRTLLRYA | Y | 1 | 88 ± 5 |
| DOUBLE SUBSTITUTIONS: | | | | | |
| [Ala$^{68,75}$]-D$^k$-(62–85) | 21 | RETQIAAGNEQSFAVDLRTLLRYY | K,R | >60 | 44 ± 6 |
| [Ala$^{69,76}$]-D$^k$-(62–8) | 22 | RETQIAKANEQSFRADLRTLLRYY | G,V | ≈30 | 42 ± 4 |
| [Ala$^{70,77}$]-D$^k$-(62–85) | 23 | RETQIAKGAEQSFRVALRTLLRYY | N,D | 7 | 72 ± 4 |
| [Ala$^{72,79}$]-D$^k$-(62–85) | 24 | RETQIAKGNEASFRVDLATLLRYY | Q,R | ≈90 | 54 ± 4 |
| [Ala$^{73,80}$]-D$^k$-(62–85) | 25 | RETQIAKGNEQAFRVDLRALLRYY | S,T | >90 | 59 ± 4 |
| OTHER PEPTIDES: | | | | | |
| HLA-A2-(69–85) | 26 | AHSQTHRVDLGTLRGYY | | Inactive$^d$ | NT |
| HLA-A2-(69–76)D$^k$-(77–85) | 27 | AHSQTHRVDLRTLLRYY | | Inactive$^d$ | NT |
| D$^k$-(69–76)HLA-A2-(77–85) | 28 | GNEQSFRVDLGTLRGYY | | Active$^d$ | NT |
| HLA-B27-(69–85) | 29 | AKAQTDREDLRTLLRYY | | Inactive | NT |
| [Phe$^{74}$]-HLA-B27-(69–95) | 30 | AKAQTFREDLRTLLRYY | | Active | NT |

Legend to Table 4

$^a$EC$_{50}$ value for glucose uptake as measured in the rat adipose cell assay.

$^b$Aggregation measured by centrifugation of 30 μM peptide solution in KRH for 10 min at 12,000 g and the amount of peptide remaining in solution determined spectrophotometrically. The numbers indicated are per cent precipitated and are mean±SEM of 3 experiments.

$^c$NT, not tested.

$^d$Maximal peptide effect in cells fully stimulated by insulin was 40% enhancement over insulin alone. Peptides peptide m is also in this category, although its activity is comparable to that of peptide b. Peptides g and q (no activity) and peptide 1 (reduced activity) have spectra with a negative maximum, no positive maximum, but with an indication of some molecules with ordered structure. Only the inactive peptides d and p have the typical spectrum of a random coil, with a negative maximum at 195 nm. The degree of ordered structure as estimated by CD and the biological activity ($\chi^2$=10.6; P<0.05) are positively correlated as determined, by a conservative test ignoring the rank order of categories in the 3×3 contingency table.

Aggregation.

Table 4 shows the extent of aggregation of the various peptides. Using scatter plot diagram analysis it is apparent that a positive correlation (r=0.56, P<0.05) exists between the biological activity of a peptide and the ability of the peptide to self-interact and form aggregates. Peptide self-interaction (aggregation) was also found to be correlated with the degree of ordered structure (r=0.49, P<0.05).

Effect of [Ala$^{85}$]-D$^k$-(65-85) Peptide In Vivo

To examine the effect of peptide on blood glucose level in vivo, 3.0 mg/kg of the [Ala$^{85}$]-D$^k$-(65-85) peptide in 0.3 ml KRH buffer was injected subcutaneously into rats. In a parallel group of animals, 0.3 ml KRH buffer wits injected subcutaneously as a negative control. Blood glucose levels were determined prior to injection and then for 330 m at 30 m intervals after injection. Values at each time point were determined from the average blood glucose level of either 6 (KRH only) or 7 (peptide) rats. The blood glucose level of rats treated with buffer alone wits not significantly affected during the time period examined. However, within 30 m blood glucose levels in rats treated with peptide dropped to approximately 70% of blood glucose levels prior to treatment and dropped its low its approximately 60% within the time period examined. Even after 330 m, blood glucose remained at significantly decreased levels (approximately 60% of blood glucose prior to treatment). These data therefore support an in vivo role for peptide-mediated modulation of surface expression of receptors.

SUMMARY

The data summarized in FIG. 1 show that the biologically active peptides must be capable of assuming an ordered structure. However, not all peptides with ordered structure are active. Thus ordered structure is necessary but not sufficient for biological activity. The systematic alanine substitutions show that residues required for full biological activity upon substitution with alanine do not necessarily affect the ordered structure. This supports the theory that the residues exclusively required for biological activity are part of the site on the peptide that interacts with a binding site in the cell membrane. FIGS. 1B and 1C further illustrate that most of the residues required for biological activity are localized on the hydrophilic (cationic) side of the peptide, assuming an α-helical structure, whereas other residues form the hydrophobic side of the helix. It should also be noted that the information obtained from the alanine scan is premised on the assumption that the function of each residue is independent of the other residues in the peptide.

The CD studies imply that peptides in ordered structure may form an α-helix or perhaps to some extent a tighter $3_{10}$ helix for the [Ala$^{85}$]-D$^k$-(65-85) peptide. Only one residue (Phe$^{74}$) seems essential for the ordered structure and thus helix formation. The significance of Phe$^{74}$ is particularly striking as its substitution with alanine not only resulted in loss of biological activity in the mouse peptide, but introduction of Phe$^{74}$ into a human sequence resulted in biological activity of an otherwise inactive peptide.

Most of the active peptides aggregate at high concentration, implying a self-interaction between peptide molecules. The helical wheel and rod of the D$^k$-(65-85) peptide in FIGS. 1B and 1C illustrate that the hydrophilic (cationic) residues are localized on one side and the hydrophobic residues on the opposite side of the α-helix. This distribution may promote intermolecular interactions, which could be of significance in the interaction between the peptides and cells. Thus, the ability of biologically active peptides to exhibit self-peptide intermolecular interactions supports the theory that peptides bind to the α-helix of the native MHC Class I molecules on the cell surface. Such binding of peptides to the MHC Class I $α_1$-helix would be analogous to self-peptide interactions since a portion of the MHC Class I $α_1$-helix is homologous to the peptide. Furthermore, native MHC Class I molecules may interact with one another to form directs, tetramers, and perhaps even larger oligomers in the membrane (Chakrabarti, et al. (1992) *Biochemistry* 31:7182–7189; Krishna, et al. (1992) *Nature* 357: 164–167).

Search of the protein sequence database showed that all MHC Class I molecules have sequence similarity greater than 70% to D$^k$-(61-85), whereas the highest similarity of a protein other than MHC Class I was only 32%. The degree of phylogenetic conservation of an amino acid residue in the MHC Class I molecule for the D$^k$-(65-85) molecule is unrelated to the importance of the residue for biological activity. However, this is not surprising as conservation of a given amino acid in different MHC Class I molecules may simply reflect a critical role of three-dimensional structure. Here, the biological activity is related to inhibition of receptor internalization. The present data support that peptide activity may depend upon a direct binding of the peptide to the $α_1$ domain of MHC Class I on the cell surface. Such an interaction is analogous to the peptide-peptide self-interaction.

EXAMPLE 5

MHC Class I Peptide Inhibition of Internalization of Glucose Transporters and IGF-II Receptors Materials and Methods Glucose Transport Activity, Photoaffinity Labeling, and Immunoblotting. Briefly, adipose cells were equilibrated at 37° C. for 30 min and then incubated for an additional 30 min at 37° C. with buffer (basal), 10 µM D$^k$-(62-85), 150 nM insulin (which induces maximal stimulation of both glucose transporter and IGF-11 receptor translocation to the cell surface (Appell, et al. (1988) *J. Biol. Chem.* 263:10824–10829), or 150 nM insulin plus 10 µM D$^k$-(62-85). 3-O-methylglucose transport was measured according to the method of Karnieli, et al. (1981) *J. Biol. Chem.* 256:4772–4777. Photoaffinity labeling wits carried out by mixing 2.5 ml of cell suspension with 500 µCi 2-N-4(1-azi-2,2,2-trifluoroethyl)benzoyl-1,3-bis(D-mannos-4-yloxy)-2-propylamine (ATB-[2-$^3$H]-BMPA) and immediately exposing the cells to UV irradiation for 3×1 min. The cells were then washed and solubilized in phosphate-buffered saline containing 2% Thesit (Boehringer Mannheim), 5 mM EDTA, 2 mM N-ethylmaleimide, 1 mM phenylmethylsulfonyl-fluoride, 1 µg/ml each of pepstatin, leupeptin, aprotinin, and α2-macroglobulin, and the solubilized material was immunoprecipitated first with anti-GLUT4 antiserum and protein-A agarose (21), and subsequently with anti-GLUT1 antiserum. Polyclonal antisera to the synthetic peptide antigens (provided by Hoffman-La Roche) was raised in rabbits. The labeled proteins in the precipitates were separated by 10% SDS-PAGE, each lane was cut into 3 mm slices, and the slices were processed for scintillation counting.

For immunoblotting, 5 ml of cells were used for preparation of plasma membrane (PM) and low-density microsomes (LDM) as described (Simpson, et al. (1983) *Biochim. Biophys. Acta.* 763:393–407). Recovery of the membrane fractions was determined by measuring protein (bicinchoninic acid assay, Sigma), and 50 μg of protein were run on 10% SDS-PAGE, transferred to nitrocellulose, and immunoblotted with antisera against GLUT1, GLUT4, or IGF-II receptors (the latter kindly provided by Dr. Robert C. Baxter, University of Sydney, Australia) followed by $^{125}$I-labeled protein-A. The radioactive bands on the nitrocellulose were excised and counted in a γ-counter. Control experiments using SDS-PAGE analysis of proteins from subcellular fractionation of adipose cells treated with buffer, peptide, insulin, or insulin plus peptide show that the peptide does not affect the overall protein distribution within the various subcellular fractions.

Cross-linking and Binding or IGF-II.

For cross-linking of $^{125}$IGFI-I I, cells were incubated with or without $D^k$-(62-85) peptide and with or without insulin as described above, followed by a 30-min incubation with 250 pM $^{125}$I-labeled IGF-II (2,000 Ci/mmol, Amersham) in the absence or presence of 100 nM unlabeled IGF-II. Cells were isolated on oil and transferred to albumin-free incubation buffer containing 1 mM disuccinimidyl suberate (Pierce) and incubated for 10 min at 16° C. The cells were solubilized in sample buffer and run on 10% SDS-PAGE. The IGF-II receptor was identified by autoradiography and quantitated by counting the excised bands.

For competition binding curves, cells were preincubated as described and then incubated for an additional 30 min with 8 nM insulin or 8 nM insulin plus 10 μM $D^k$-(62-85) peptide. KCN was added to a final concentration of 2 mM and the incubation wits continued for another 15 min. Subsequently, the cells were washed and resuspended in buffer with 2 mM KCN: 50 μl of cells were mixed with 50 μl of $^{125}$I-labeled IGF-II (final concentration 50 pM) in the absence or presence of various concentrations of non-radioactive IGF-II (Sigma) and further incubated for 30 min at 37° C. before harvesting the cells on oil. Acid wash of cells incubated with $^{125}$I-IGF-II in the presence or absence of KCN showed that KCN effectively blocks 85–90% of receptor internalization. Thus, whole cell binding in the presence of KCN reflects surface-bound IGF-II.

Kinetics of internalization of GLUT4 and IGF-II Receptors.

Adipose cells were preincubated as described and incubated an additional 30 min at 37° C. with 8 nM insulin in the absence or presence of 20 μM [Ala$^{85}$]-$D^k$-(69-85). For GLUT4 experiments, 4.0 ml volumes of cells were then photolabeled with 750 μCi ATB-[$^3$H]-BMPA as described above except that UV irradiation was limited to 2×30 s and the cells were further protected from radiation damage by covering the samples with plastic lids. Photolabeled cells were subsequently incubated for an additional 0, 10, 20, 30, or 60 min. At each time point, samples were taken for measurement of glucose transport activity, KCN was added to the remaining cells to a final concentration of 2 mM to arrest subcellular trafficking, the cells were harvested, and PM and LDM were prepared. The amounts of radiolabeled GLUT4 in PM and LDM were determined by immunoprecipitation as described above. For IGF-II receptors, $^{125}$I-IGF-II was added to 50 pM to insulin- or insulin plus peptide-stimulated cells in the presence or absence of 50 nM unlabeled IGF-II in a final volume of 100 μl and the cells were harvested after 5, 10, 15, 20, 30, or 60 min incubation. Upon harvest, the cells were transferred to 100 μl buffer at either pH 7.2 or pH 2.0 (final pH 3.0), incubated on ice for 5 min, and harvested by centrifugation on oil. Internalized IGF-II was defined as specific acid resistant $^{125}$I.

Peptides.

$D^k$-(61-85) (ERETQIAKGNEQSFRVDLRTLLRYY) (SEQ. ID NO: 31) was used in previous studies. However, in the present study an N-truncated version of the peptide, $D^k$-(62-85), with the same potency was used because the N-terminal Glu$^{61}$ residue of $D^k$-(61-85) is a potential source of peptide heterogeneity due to possible cyclization to poly-glutamic acid (pGlu). For kinetic studies, [Ala$^{85}$]-$D^k$-(65-85) was used instead of $D^k$-(62-85) because it is as potent as $D^k$-(62-85) but poses fewer technical difficulties in handling. Synthesis, purification, and methods to assure the correct identity of the peptides were performed as described above. The $D^k$-(62-85) peptide used in the present study was maintained in an active conformation by incubation of 1 mM stock solution at 37° C. in 0.1M NaCl overnight, whereas [Ala$^{85}$]-$D^k$-(65-85) was used directly from a 1 mM stock solution in water.

RESULTS

Glucose Transport Activity and Photolabeling with ATB-BMPA.

Table 5 shows that the $D^k$-(62-85) peptide enhances 3-O-methylglucose transport by about 2-fold in the absence of insulin in rat adipose cells, corresponding to an increment of 0.15 fmol/cell/min. In insulin-stimulated cells, peptide also enhances glucose transport activity by about 2-fold, but with a much larger absolute effect (4.0 fmol/cell/min). Further, photolabeling with ATB-[2-$^3$H]-BMPA shows that insulin stimulation increases cell surface GLUT4 by 27-fold compared to basal whereas $D^k$-(62-85) plus insulin results in a 42-fold increase. Thus, the $D^k$-(62-85) effect on enhancement of glucose transport activity corresponds well to the increase in GLUT1 in either the absence or presence of insulin.

TABLE 5

| | EXPERIMENTAL GROUPS | | | |
|---|---|---|---|---|
| | Basal | $D^k$-(62-85) | Insulin | Insulin + $D^k$-(62-85) |
| 3-O-methyl-glucose transport (fmol per cell per min) | 0.11 ± 0.03 | 0.26 ± 0.05 | 4.1 ± 0.3 | 8.1 ± 0.7 |
| ATB-BMPA cross-linking ($^3$H dpm per 10$^6$ cells) GLUT1 | 0.10 ± 0.03 | 0.12 ± 0.01 | 0.32 ± 0.05 | 0.36 ± 0.05 |
| GLUT4 | 0.17 ± 0.02 | 0.35 ± 0.1 | 4.7 ± 0.4 | 7.2 ± 0.5 |

IGF-II Binding and Cell Surface IGF-II Receptors.

Figure 2A:
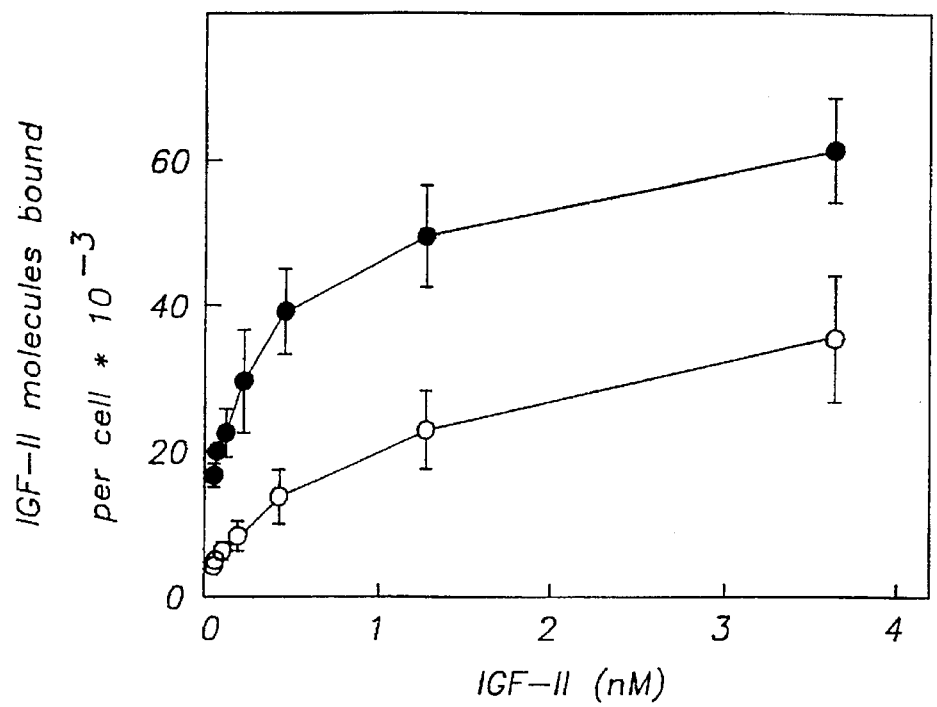
FIGS. 2A and B. Effect of $D^k$-(62-85) on IGF-II cross-linking and binding to rat adipose cells. Isotherm and competition binding curves of $^{125}$I-IGF-II ligand in the presence (solid circles) or absence (open circles) of 10 µM $D^k$-(62-85) are presented in panels A and B, respectively.
Figure 2B:
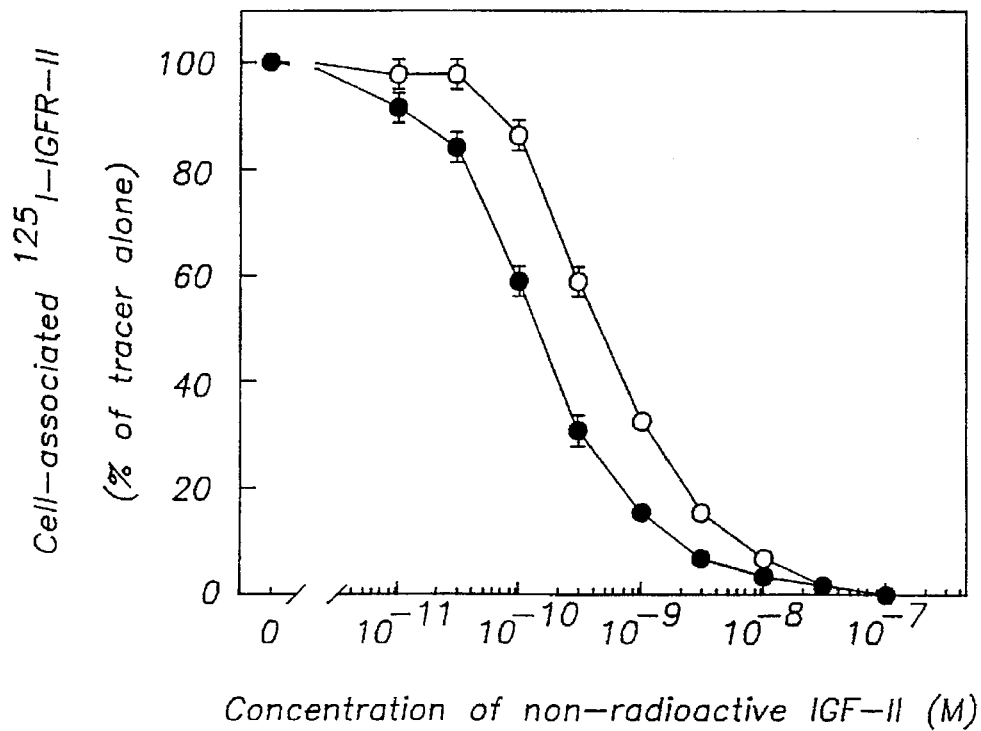

Table 6 illustrates that $D^k$-(62-85) augments cell surface IGF-II binding 5–6-fold in rat adipose cells both in the absence and presence of insulin, as identified by cross-linking of $^{125}$IGF-II. Further, the isotherm and competition binding curves in FIG. 2 demonstrate that the increase in the binding of IGF-II is due to a doubling of the number of IGF-II receptors on the cell surface and an apparent change in the affinity of IGF-II receptors for ligand binding from 419±71 pM in insulin-treated cells to 145±20 pM in cells treated with insulin plus peptide (means±standard error of 7 experiments: P<0.05; Student t-test).

TABLE 6

| EXPERIMENTAL GROUPS | | | | |
|---|---|---|---|---|
| | Basal | $D^k$-(62-85) | Insulin | Insulin + $D^k$-(62-85) |
| IGF-II cross-linking (fmol per $10^6$ cells) | 0.7 ± 0.2 | 3.5 ± 0.6 | 1.7 ± 0.4 | 11.7 ± 2.9 |

Immunoblotting of Glucose Transporters and IGF-II Receptors in Subcellular Membrane Fractions.

In contrast to the GLUT4 photolabeling results, analysis of the subcellular distribution of GLUT4 by immunoblotting did not reveal any detectable effect of $D^k$-(62-85) in the absence of insulin (Table 7). In the presence of insulin, the peptide enhanced the insulin-stimulated depiction of GLUT4 in LDM, but a corresponding increase of GLUT4 in PM is not observed. Subsequent studies on the subcellular distribution of photolabeled GLUT4, i.e. cell surface GLUT4, compared to that of immunodetectable GLUT4, indicated that the peptide-mediated increase of GLUT4 on the cell surface in intact cells was accompanied by an increase in GLUT4 associated with other subcellular fractions, in particular the fat cake and nuclear membranes. This is likely to explain the lack of an immunodetectable increase in GLUT4 in PM. Similarly, immunoblotting with an IGF-II receptor-specific antiserum demonstrated a reduction in the microsomal concentration of IGF-II receptors in cells treated with insulin plus peptide compared to insulin alone. However, again a corresponding increase in IGF-II receptors in PM is not observed.

TABLE 7

| EXPERIMENTAL GROUPS | | | | |
|---|---|---|---|---|
| | Basal | $D^k$-(62-85) | Insulin | Insulin + $D^k$-(62-85) |
| GLUT1 | | | | |
| PM | 2.6 ± 0.1 | 3.0 ± 0.1 | 5.6 ± 0.2 | 5.8 ± 0.1 |
| LDM | 5.1 ± 0.4 | 4.8 ± 0.6 | 1.3 ± 0.1 | 1.0 ± 0.1 |
| GLUT4 | | | | |
| PM | 0.2 ± 0.1 | 0.3 ± 0.1 | 1.2 ± 0.1 | 1.3 ± 0.2 |
| LDM | 1.7 ± 0.2 | 1.8 ± 0.4 | 1.0 ± 0.3 | 0.6 ± 0.1 |
| IGF-II Receptor | | | | |
| PM | 0.3 ± 0.0 | 0.4; 0.4 | 0.5; 0.5 | 0.7 ± 0.1 |
| LDM | 2.1 ± 0.1 | 2.0 ± 0.2 | 2.0 ± 0.1 | 1.3 ± 0.1 |

It has previously been described that the insulin-induced enhancement of the number of GLUT4 in the plasma membrane appears lower when measured with immunoblotting as compared to photolabeling with ATB-BMPA (Holman, et al. (1990) *J. Biol. Chem.* 265:18172–18179). Indeed the increase in GLUT4 in the plasma membrane induced by insulin plus peptide is 42-fold as measured by fluorescent labeling, whereas the corresponding immunoblotting data only suggest a 2.3-fold increase, i.e. again the latter is only 14% of the former. Part of the reason for the lower effect as measured by immunoblotting may be that the subcellular fractionation procedure results in cross-contamination of PM with LDM, thus inflating the levels of GLUT4 and IGF-II receptors in PM in the basal site and reducing the apparent fold-response to insulin.

Kinetics of GLUT4 and IGF-II Receptor Internalization.

Figure 3:
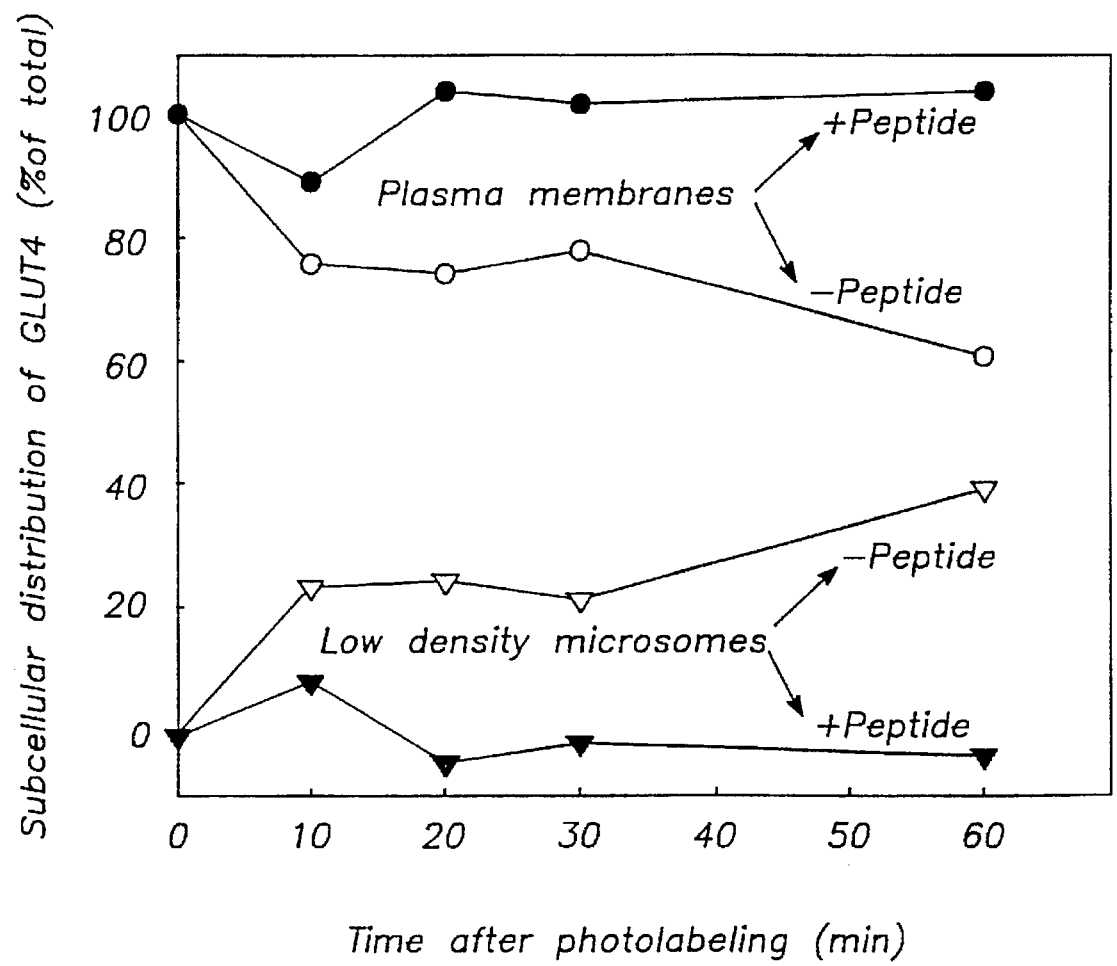
FIG. 3. Effects of [Ala$^{85}$]-$D^k$-(65-85) on the kinetics of GLUT4 internalization in rat adipose cells.
Figure 4B:
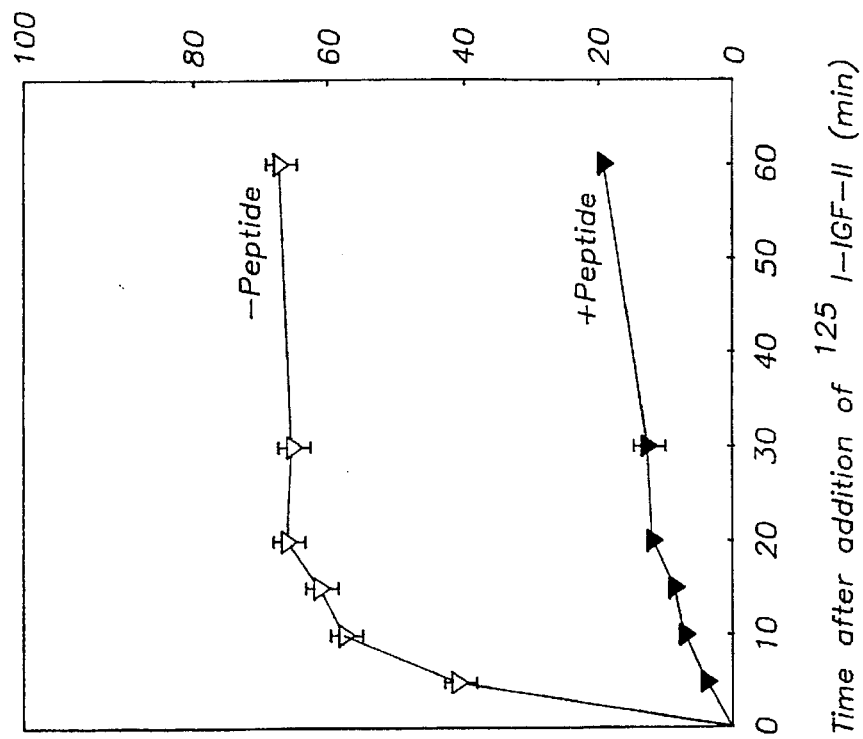
FIGS. 4A and B. Effects of [Ala$^{85}$]-$D^k$-(69-85) on the kinetics of the IGF-II receptor internalization in rat adipose cells.
Figure 4A:
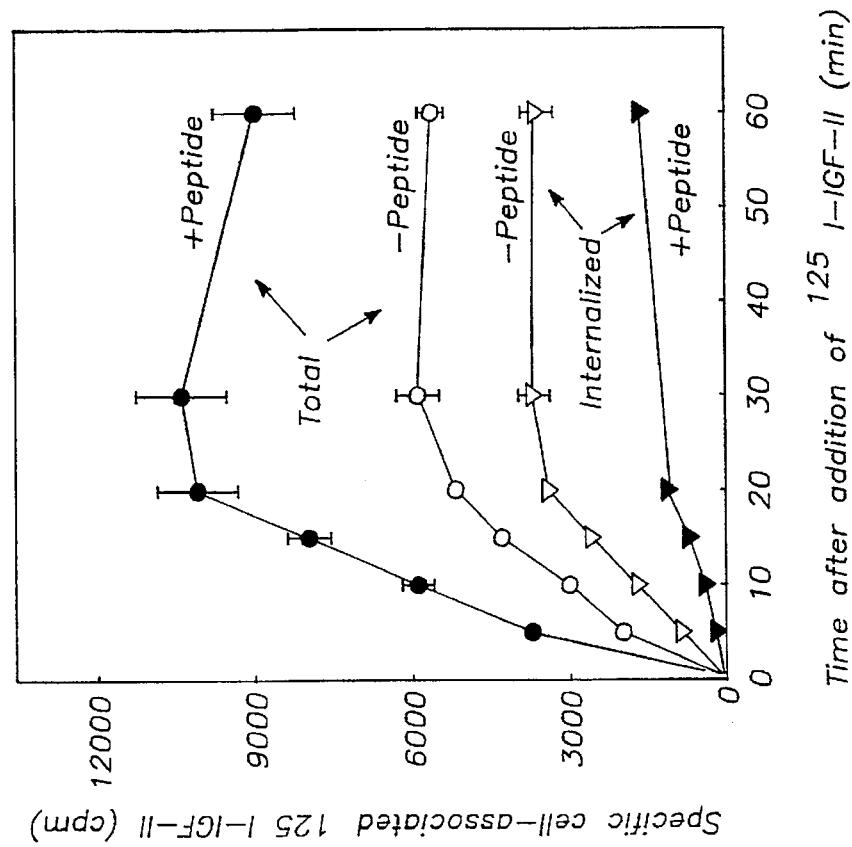

The [Ala$^{85}$]-$D^k$-(65-85) peptide completely inhibited the appearance of photolabeled GLUT4 in LDM as compared to cells treated with insulin alone. The rate of internalization of GLUT4 in cells stimulated with insulin is 15±4% per hr of cell surface radiolabeled GLUT4 (calculated from 6 time points in two independent experiments) and significantly (P<0.05) reduced to 0±4% per hr in insulin plus peptide-treated cells (FIG. 3). [Ala$^{85}$]-$D^k$-(65-85) also had a marked inhibitory effect (about 80%) on the rate of internalization of IGF-II receptors in insulin-stimulated cells (FIG. 4)

EXAMPLE 6

MHC Class I Peptide Recommendation of IGF-I Receptor

Materials and Methods

Cell line.

CHO cells over-expressing human IGF-I receptor (approximately 2×10$^5$ receptors per cell) were generated by transfecting the cells with the expression vector RLDN containing the full length IGF-1 receptor cDNA. The transfected cells were selected with 400 µg/ml G418, and the cell line overexpressing IGF-1 receptors was identified by a standard IGF-1 ligand binding assay. The cells were grown in Ham's F12 medium supplemented with 10% fetal calf serum.

Ligand internalization.

Sub-confluent cells in 35 mm wells were used. The monolayer was washed twice with phosphate buffered saline (PBS) and once with KRP-Hepes binding buffer (pH 7.5) at room temperature. The cells were incubated in 1 ml of binding buffer containing 1 µg/ml $^{125}$I-IGF-I at 37° C. for 20 min. At the end of the incubation, the cells were washed 3 times with cold PBS and the surface-bound ligand was extracted with acidic binding buffer (pH 3.5) for 5 min at 4° C. After acid extraction, the cell associated radioactivity was determined by lysing the cells with 0.4N NaOH and used as a measure of internalized ligand. The percent of ligand internalization was calculated by dividing the internalized cpm by surface bound pills internalized cpm. In each experiment, 500 ng/ml of des-IGF-1 was added to separate wells to determine the amount of ligand bound to non-receptor sites and was subtracted from the surface or internalized cpm. Des-IGF-1 is an analog of IGF-1 with the three amino acids at the N-terminal deleted. As a result, Des-IGF-1 binds normally to IGF-1 receptors, but binds to IGF binding proteins with a very low affinity.

RESULTS

Ligand internalization.

When cells are incubated with $^{125}$I-IGF-1, in the presence or absence of 30 µM $D^k$-(62-85), and ligand internalization measured by the acid extraction technique, the peptide leads to a marked decrease in internalized $^{125}$I-IGF-1 with a corresponding increase in surface bound hormone (FIG. 5). When the percent $^{125}$I-IGF-1 internalized was calculated, $D^k$-(62-85) resulted in a 43.9±1.7% decrease (P<0.01) in ligand internalization. This inhibitory effect was dose dependent with half maximal effects at 8 µM and maximal inhibition of internalization at 30 µM.

EXAMPLE 7

Inhibition of Internalization of Transferrin Receptor

Materials and Methods

Rat adipocytes (100 µl at 31% lipocrit) were incubated in KRHB (5% BSA) in minisorp tubes at 37° C. for 30 min. In test samples, activated $D^k$[62-85] peptide was added to a final concentration or 30 μM. Incubation of both test samples containing peptide, as well as control samples without peptide, was continued lot 60 min at 37° C. $^{125}$I-transferrin (approximately 25,000 cpm/tube) was added to 2 nM with or without 200 nM unlabeled competitor. Incubation at 37° C. continued or 10 min. The cells were diluted twofold with cold KRHB (5% BSA) at pH 7.4 or pH 1.8 and held once for 10 min. Finally, the cells were separated from the supernatant by centrifugation through oil and the number of specific counts determined using a gamma scintillation counter. Data are represented as the mean and standard error among three replicates and present as 10 minute counts (Table 8).

Table 8. Specific Binding and Internalization of $^{125}$I-Transferrin to Rat Adipocytes

| $D^k$[62-85] Peptide | Specific Counts | | | Fold Increase In Extracellular, Bound Transferrin with Peptide |
|---|---|---|---|---|
| | Total | Internalized | Percent Internalized | |
| − | 649 ± 21 | 269 ± 36 | 41.1 | 1.86 |
| + | 1204 ± 53 | 131 ± 25 | 10.6 | |

Figure 6:
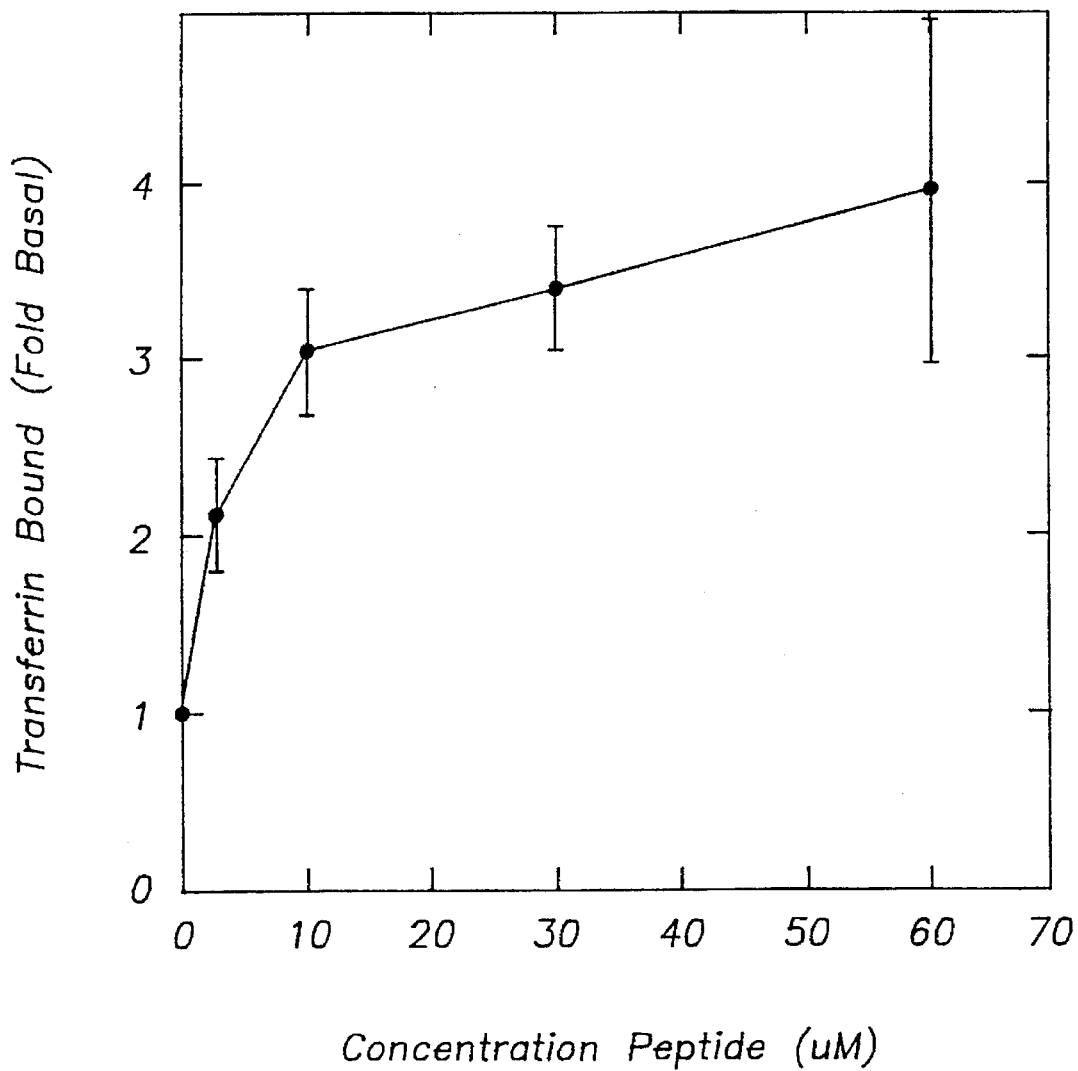
FIG. 6. Effect of $D^k$-(62–85) peptide on binding of labeled transferrin to rat adipose cells.

Using the protocol described above, the effect of the $D^k$[62-85] peptide on the binding of labeled transferrin to rat adipocytes was determined as a function of peptide concentration. The results are expressed Its the fold difference between the amount of transferrin bound in the presence of peptide over the amount of transferrin bound in the absence of peptide. As can be seen in FIG. 6, the amount of bound transferrin increases with an increase in the concentration of peptide added up to an approximate concentration of 10 μM peptide.

For experiments using human fibroblasts, approximately $10^5$ human fibroblasts were plated in wells of 24 well plates. Before performing the binding assay, the media was removed and replaced with KRHB (1% BSA). Plates were incubated at 37° C. for 1 hr. Activated peptide at 30 μM was added where indicated and incubation proceeded for another 1 hr period at 37° C. Finally $^{125}$I-transferrin was added (approximately 25,000 cpm/well) at a concentration of 2 nM, with or without 1 μM unlabeled competitor. Incubation at 37° C. continued for 15 min. The labeling solution wits removed and replaced with an excess of ice-cold KRHB (1% BSA) at pH 7.4 or pH 3.7. The plates were then held on ice for 5 min. The cells were solubilized with 0.1N NaOH and counted. Data are represented as the mean and standard error among three replicates and presented as 1 minute counts (Table 9).

TABLE 9

Specific Binding and Internalization of $^{125}$I-Transferrin to Human Fibroblasts

| $D^k$[62-85] Peptide | Specific Counts | | | Fold Increase In Extracellular, Bound Transferrin with Peptide |
|---|---|---|---|---|
| | Total | Internalized | Percent Internalized | |
| − | 179 ± 26 | 107 ± 39 | 59.8 | 1.97 |
| + | 353 ± 19 | 106 ± 12 | 30.0 | |

Using the same assay protocol its described above for rat adipocytes, the extent of surface binding of $^{125}$I-labeled transferrin to human fibroblasts was determined in either the presence or absence of 30 μM as a function of transferrin concentration. The results are expressed as a percent bound of total added transferrin In the absence of the peptide, transferrin binds with an $EC_{50}$ of 18.1 nM. In contrast, in the presence of 30 BM peptide, transferrin binds with an $EC_{50}$ of 17.2 nM. Therefore, the peptide has no affect on the binding affinity of transferrin to its receptor.

EXAMPLE 8

MHC Class I Peptide Regulation of Low-Density Lipoprotein (LDL) Receptor

The effect of the [Ala$^{85}$]$D^k$(65-85) MHC Class I peptide on the low-density lipoprotein (LDL) receptor in human fibroblasts was examined. Human foreskin fibroblasts were seeded in 24-well tissue culture plates with 10,000 cells per well and incubated in RPMI-1640 medium containing 10% FCS overnight. The cells were then washed in KRH and incubated for 1 hr in KRH containing 5% BSA in the absence or presence of 10 μM of [Ala$^{85}$]$D^k$(65-85) peptide. After incubation, the wells were washed with ice-cold KRH, anti-LDL antibody added and the samples incubated at room temperature for 1 hr. The plates were then again washed, $^{125}$I-protein A added in KRH containing 5% BSA. Following incubation for 1 hr at room temperature, unbound $^{125}$I-protein A was removed with 3 washes with KRH, the cells harvested by trypsinization for 15 min at room temperature and the amount of bound $^{125}$I determined in a gamma counter. Data from these experiments, each performed in triplicate, are presented in Table 10. As shown, surface expression of LDL receptor is significantly enhanced in the presence of peptide.

TABLE 10

Specific Anti-LDL Receptor Antbody Binding to the Cell Surface of Human Fibroblasts

| Peptide | Mean ± SEM (per 10,000 cells) |
|---|---|
| − | 249 ± 243 |
| + | 1948 ± 213 |

Figure 7:
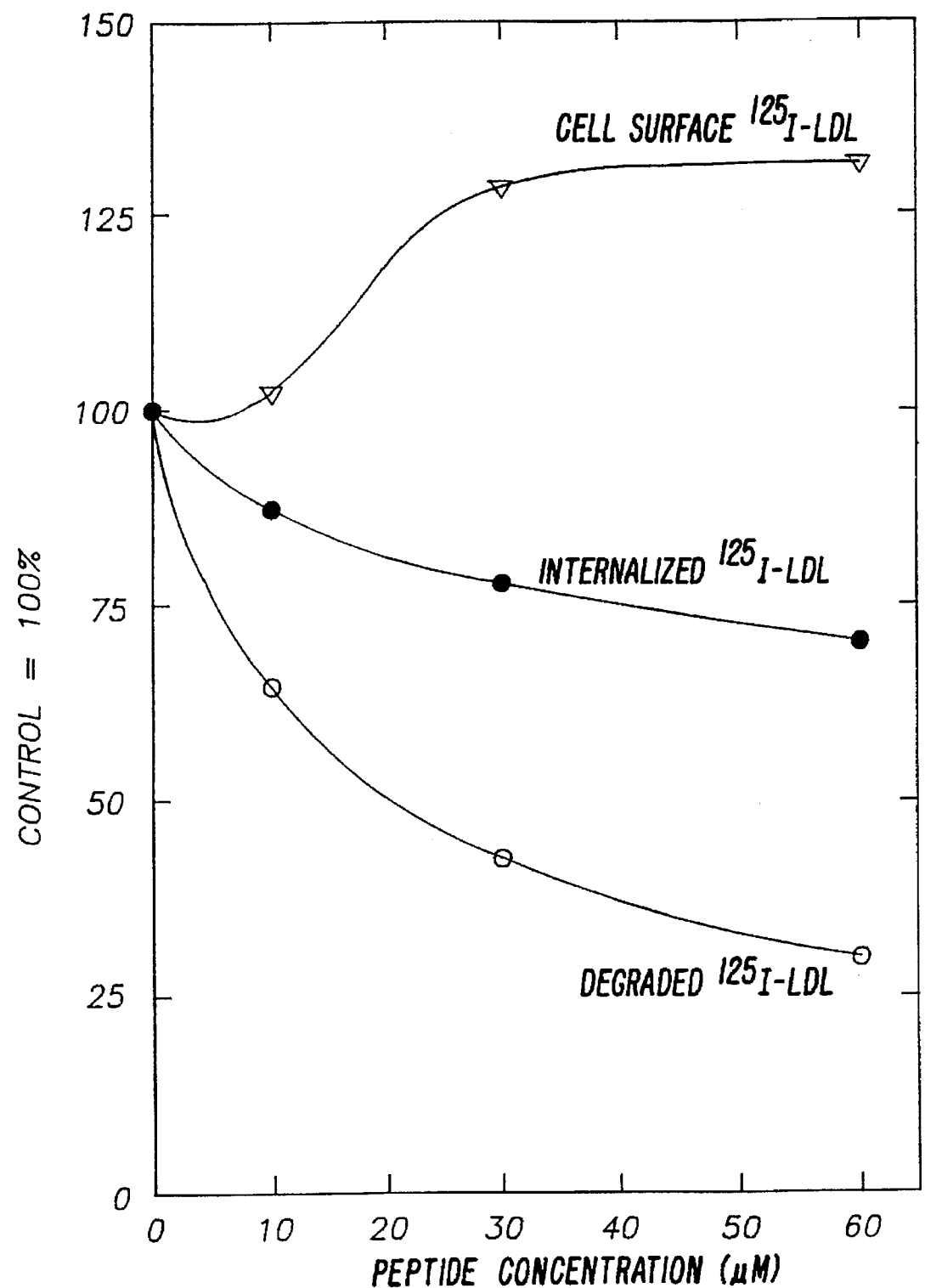
FIG. 7. Effect of [Ala$^{85}$]-$D^k$-(69-85) peptide on the subcellular localization of low-density lipoprotein receptor in human fibroblasts.

To determine whether increased surface expression was due to an overall increase in the number of LDL receptors in the cell or an inhibition of internalization of the receptor, the relative amounts of cell surface, internalized, and degraded LDL were examined as a function of peptide concentration. Normal human fibroblasts were seeded in 6-well tissue culture plates at 10,00 cells/well in 2.0 ml DMEM medium containing 10% FCS. After overnight incubation, the cells were washed in DMEM with 2% BSA and $^{125}$I-LDL added in the absence or presence of various concentrations of [Ala$^{85}$]$D^k$(65-85) peptide. Following incubation for 5 hr at 37° C., the relative amounts of cell surface and internalized LDL receptors in untreated cells were determined as the amount of dextran sulfate soluble and dextran sulfate resistant $^{125}$I-LDL respectively, the amount of degraded LDL receptors was determined by detecting the amount of $^{125}$I-monotyrosine in the culture medium. All values obtained in samples containing peptide were set relative to samples prepared in the absence of peptide. As shown in FIG. 7, the amount of cell surface LDL significantly increased with an increase in peptide concentration up to a maximum surface expression (about 1.5 fold higher than controls) in the presence of about 30 μM peptide. Concurrently, the amount of internalized and degraded LDL decreased with increasing peptide concentration. Thus, the increase in surface expression of LDL receptors in the presence of peptide is a result of the inhibition of internalization of the receptor.

EXAMPLE 9

MHC Class I Peptide Regulation of the LDL "Scavenger" Receptor

The effect of [Ala$^{85}$]D$^k$(65-85) on internalization of the LDL scavenger receptor was examined in the murine macrophage cell line J774. Macrophages were incubated for 2 hr at 37° C. in DMEM with 2% BSA with $^{125}$I-acetylated-LDL (±dextran sulfate) in the absence or presence of peptide. The amount of specific binding of labeled LDL was determined by the ability of unlabeled LDL to compete away bound labeled LDL. The amounts of cell-associated and degraded LDL in the medium were determined as described above in Example 8. The results presented in Table 11 are the mean±SEM of three experiments performed with triplicate samples.

TABLE 11

| | Cell-Associated LDL | | | Degraded LDL | | |
|---|---|---|---|---|---|---|
| Peptide | Labeled | Labeled Remaining After Competition with Unlabeled | Specific | Labeled | Labeled Remaining After Competition with Unlabeled | Specific |
| − | 100 | 27 ± 5 | 73 | 100 | 48 ± 6 | 52 |
| + | 97 ± 9 | 20 ± 3 | 77 | 38 ± 3 | 42 ± 6 | −4 |

Thus, in the presence of peptide, the amount of LDL associated with the cell remains essentially the same: however, the level of LDL, degradation is significantly decreased in the presence of peptide. These data imply that, as for other receptors described above, [Ala$^{85}$]D$^k$(65-85) peptide increases the population of LDL receptors on the cell surface.

EXAMPLE 10

Effect of MHC Class I Peptide on β$_2$-Adrenergic Receptor (β$_2$AR)

Chinese hamster ovary (CHO) cells expressing β$_2$AR were incubated in DMEM with 5% FCS in the absence or presence of 30 µM of the [Ala$^{85}$]-D$^k$(65-85) peptide. The media was then supplemented with 5 µM isoproterenol to induce β$_2$AR internalization. Incubation was continued for 0, 7, 20 and 60 min and then terminated by washing the cells with ice cold PBS. The cells were collected and subjected to a ligand binding assay utilizing $^{125}$I-iodopindolol in the presence of 0.4 mM of a hydrophilic propanol derivative (e.g. CGP, a hydrophilic ligand used to label cell surface receptors). Ligand binding, as reflected by the distribution of receptors in the plasma membrane versus internalized receptors, was determined. The amount of ligand binding was determined to the same in both untreated control cells and cells exposed to peptide. Thus the surface expression and internalization of β$_2$AR is unaffected by the presence of peptide.

EXAMPLE 11

Effect of Antibody to MHC Class I on Glucose Uptake and Peptide Binding

The antibody Ox-18 [Sigma, St. Louis] has binding specificity for Class I MHC antigen of rats. The effect of this antibody on glucose uptake in rat adipose cells was examined. Rat adipose cells were prepared and seeded for assays as described in Example 4. Briefly, rat adipose cells were obtained from epididymal fat pads and suspended in Krebs-Ringer HEPES buffer (KRH) with 5% bovine serum albumin at a lipocrit of 10% (final). The effect of the antibody was measured in cells maximally stimulated with insulin (8 nM). After equilibration at 37° C. for 30 min the cells were incubated for 30 min at 37° C. with buffer (basal), 8 nM insulin plus varying concentrations of Ox-18 antibody. Samples containing 8 nM insulin pills either 30 µM [Ala$^{85}$]-D$^k$(65-85) peptide or 6 µg/ml Ir. Ab, an anti-mouse K$^k$ Class I MHC antibody, were included as positive and negative controls, respectively. $^{14}$C-D-glucose was added, the cells were incubated for an additional 30 min, harvested on oil and counted in a scintillation counter. All values were expressed relative to the basal level of glucose uptake.

In the presence of 30 mM [Ala$^{85}$]-D$^k$(65-85) peptide, glucose uptake levels were 60% over the basal levels while the anti-mouse MHC class I antibody had no affect on glucose uptake. However, the Ox-18 antibody significantly affected glucose uptake, with the increase of glucose uptake relative to basal levels increasing with increasing concentration of antibody to a maximal stimulation of glucose uptake at about 60% above basal levels. These data support the theory that this anti-MHC Class I antibody and the [Ala$^{85}$]-D$^k$(65-85) stimulate glucose uptake by similar mechanisms.

In similar assays the effect of incubation with [Ala$^{85}$]-D$^k$(65-85) peptide and the Ox-18 antibody either alone or in combination on the glucose uptake level of rat adipocytes was examined. The protocol described fo the antibody experiments above was again employed. However, in these experiments, the following samples were prepared: no peptide (basal level control), 30 µM activated [Ala85]-D$^k$(65-85) peptide plus 8 nM insulin, 2 µg/ml Ox-18 antibody plus 8 nM insulin, 30 µM activated [Ala85]-D$^k$(65-85) peptide pills 2 µg/ml Ox-18 antibody plus 8 nM insulin, and 2 µg/ml Ir.Ab (anti-mouse K$^k$ Class I MHC antibody) plus 8 nM insulin. The results, presented in Table 12, are expressed as a percent of the basal level of glucose uptake.

TABLE 12

Effect of Antibody to MHC Class I (Ox-18) on Glucose Uptake and $^{125}$I-[Ala85]-D$^k$(68-85) Peptide Binding in Rat Adipose Cells

|  | Basal Level | Peptide (30 µM) | Ox-18 (2 µg/ml) | Peptide + Ox-18 | Ir.Ab (2 µg/ml) |
|---|---|---|---|---|---|
| Glucose Uptake | 100 | 139 ± 10 | 142 ± 7 | 161 ± 7 | 102 ± 4 |
| Specific Binding of Peptide | 100 | 0 | 19 ± 4 | 0 | 93 ± 8 |

As seen above, [Ala$^{85}$]-D$^k$(65-85) peptide and Ox-18 enhanced glucose uptake levels to similar levels. However, in samples containing both peptide and Ox-18 antibody, glucose uptake levels were only slightly enhanced relative to peptide alone or antibody alone. Thus, these data imply that peptide and Ox-18 antibody act by similar mechanisms and are competing for sites of action.

To examine the possibility that the [Ala$^{85}$]I-D$^k$(65-85) peptide and Ox-18 antibody share the same or similar binding sites, a competitive binding assay with rat adipose cells was performed. The samples described above were again prepared. Rather than adding $^{14}$C-D-glucose, $^{125}$I-[Ala$^{85}$]-D$^k$(65-85) (approximately 25,000 cpm/sample) was added to a concentration of 30 gM to all samples. Incubation at 37° C. continued for 10 min. The cells were diluted twofold with cold KRHB (5% BSA) at pH 7.4 or pH 1.8 and held once for 10 min. Finally, the cells were separated from the supernatant by centrifugation through oil and the number of specific counts determined using a gamma scintillation counter. All values were set relative to specific binding of peptide in the basal level samples (100%). As seen from the data in Table 12, the presence of the control antibody, Ir.Ab had no significant effect on the binding of labeled peptide. In contrast, the Ox-18 antibody reduced the specific binding of labeled peptide to only about 19% of control levels. While binding of the [Ala85]-D$^k$(65-85) peptide was not completely inhibited by the Ox-18 antibody, this significant reduction of binding suggests that the antibody and the peptide competitively bind for similar sites.

It is evident from the above results that surface membrane receptors, particularly those receptors inactivated by internalization and involving transduction of signals as exemplified by the insulin receptor, EGF receptor, IGF-I receptor, IGF-II receptor, LDL receptor and LDL scavenger receptor are modulated by MHC Class I antigen and peptides derived therefrom, particularly H-2D and -L of mice and HLA-B and -C of humans. A wide variety of physiological processes, both in vitro and in vivo, may be regulated by controlling the interaction between the appropriate Class I antigen and the surface membrane receptor, by a variety of techniques which allow for the enhancement or reduction of the interaction between the Class I antigen and the surface membrane receptor.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for modulating a surface receptor response of a mammalian cell, wherein said surface receptor response is modulated by interaction with a Class I major histocompatibility complex antigen, said method comprising:

adding to said mammalian cell an agent capable of modulating the interaction between (1) a mammalian major histocompatibility complex Class I antigen and (2) said surface receptor on said cell;

wherein said agent is an oligopeptide of from 8 to 40 amino acids comprising as the C-terminal sequence a continuous sequence contained within the following sequence:

G N aa$^{71}$ Q aa$^{73}$ F R aa$^{76}$ aa$^{77}$ aa$^{78}$ R T aa$^{81}$ L R Y X (SEQ ID NO:32)

wherein
aa$^{71}$, if present, is G, A, S, T, D or E;
aa$^{73}$, if present, is S, T, F, Y, H or W;
aa$^{76}$, if present, is an aliphatic amino acid other than basic of from 4 to 6 carbon atoms or alanine;
aa$^{77}$, if present, is a polar aliphatic amino acid of from 3 to 6 carbon atoms or alanine;
aa$^{78}$ is a non-polar aliphatic amino acid of from 3 to 6 carbon atoms; and
aa$^{81}$ is G, L, I or V;
wherein X is an amino group to provide an amide terminal group, or the amino acids alanine or tyrosine terminating in a carboxy group;
said oligopeptide terminates in RYX; and said surface receptors are characterized by being internalized or recycled; and
whereby said receptor response is modulated with the proviso that if said surface receptor is the insulin receptor, then said agent is not an oligopeptide consisting of at least eight amino acid residues of the MHC Class I-derived sequence NH2-W-E-R-E/I-T-Q-I-A-K-G-N/Q-E-Q-S/W-F-R-V-D/N-L-R-T-L-L-R-Y-Y-COOH (SEQ ID NO: 3 with the instantly recited substitutions), wherein said MHC Class I-derived sequence comprises at least the amino acid residues L-R-T-L-L-R-Y (SEQ ID NO:36).

2. A method according to claim 1, wherein said agent affects the number of said receptors on the surface of said cell.

3. A method according to claim 1, wherein said receptor is internalized.

4. A method according to claim 1, wherein said oligopeptide comprises the identical amino acid sequence as an $\alpha_1$ domain of a human or mouse major histocompatibility complex Class I antigen.

5. A method according to claim 4, wherein the amino acid sequence of said oligopeptide comprises the sequence of amino acids from amino acid 55 to 85 of said MHC Class I $\alpha_1$ domain.

6. A method according to claim 4, wherein X is tyrosine.

7. A method according to claim 4, wherein X is alanine.

8. An oligopeptide of from 8 to 40 amino acids comprising as a C-terminal sequence a sequence of the $\alpha_1$ domain of a human or mouse major histocompatibility complex Class I antigen comprising a continuous sequence contained within the following sequence:

G N E Q aa$^{73}$ F R aa$^{76}$ aa$^{77}$ aa$^{78}$ R T aa$^{81}$ L R Y X (SEQ ID NO:33)

wherein:
aa$^{73}$, if present, is S, T, F, Y, H or W;
aa$^{76}$, if present, is an aliphatic amino acid other than basic of from 4 to 6 carbon atoms;
aa$^{77}$, if present, is a polar aliphatic amino acid of from 3 to 6 carbon atoms;
aa$^{78}$ is a neutral aliphatic amino acid of from 5 to 6 carbon atoms;
aa$^{81}$ is G, L, I or V; and
wherein X is an amino group to provide an amide terminal group, or the amino acids alanine or tyrosine terminating in a carboxy group and said oligopeptide terminates in RYX.

9. An oligopeptide of from 8 to 40 amino acids comprising as a C-terminal sequence a sequence of the $\alpha_1$ domain of a human or mouse major histocompatibility complex Class I antigen comprising a continuous sequence contained within the following sequence:

W aa$^{61}$ R aa$^{63}$ T aa$^{65}$ aa$^{66}$ aa$^{67}$ K aa$^{69}$ aa$^{70}$ aa$^{71}$ Q aa$^{73}$ F R aa$^{76}$ aa$^{77}$ L R T L aa$^{82}$ aa$^{83}$ Y aa$^{85}$ (SEQ ID NO:34)

where:
aa$^{61}$, if present, is D or E;
aa$^{63}$, if present, is E, I or N;
aa$^{65}$, if present, is Q or R;
aa$^{66}$, if present, is I, N or K;
aa$^{67}$, if present, is A, C, S or M;
aa$^{69}$, if present, is G, A, T or P;
aa$^{70}$, if present, is N, Q, K, R, S or T
aa$^{71}$, if present, is G, A, S, T, D or E
aa$^{73}$, if present, is S, T or W;
aa$^{76}$, if present, is V or E;
aa$^{77}$, if present, is N, S or D;
aa$^{82}$, is L or R;
aa$^{83}$ is G or R; and
aa$^{85}$ is Y or A, and aa$^{85}$ is the terminal amino acid.

10. A method for modulating surface expression of the GLUT4 glucose transporter of a mammalian cell, said method comprising:

adding to said mammalian cell an agent capable of modulating the interaction between (1) a mammalain major histocompatibility complex Class I antigen and (2) said GLUT4 glucose transporter on said cell, wherein said agent is an oligopeptide of from 8 to 40 amino acids comprising as the C-terminal sequence a continuous sequence contained within the following sequence:

G N aa$^{71}$ Q aa$^{73}$ F R aa$^{76}$ aa$^{77}$ aa$^{78}$ R T aa$^{81}$ L R Y X (SEQ ID NO:32)

wherein
aa$^{71}$, if present, is G, A, S, T, D or E;
aa$^{73}$, if present, is S, T, F, Y, H or W;
aa$^{76}$, if present, is an aliphatic amino acid other than basic of from 4 to 6 carbon atoms or alanine;
aa$^{77}$, if present, is a polar aliphatic amino acid of from 3 to 6 carbon atoms or alanine;
aa$^{78}$ is a non-polar aliphatic amino acid of from 3 to 6 carbon atoms; and
aa$^{81}$ is G, L, I or V; and
wherein X is an amino group to provide an amide terminal group, or the amino acids alanine or tyrosine terminating in a carboxy group;
said oligopeptide terminates in RYX; and whereby said surface expression of the GLUT4 glucose transporter is regulated.

11. A method according to claim 10, wherein said oligopeptide has the same amino acid sequence as an $\alpha_1$ domain of a human or mouse major histocompatibility complex Class I antigen.

12. A method according to claim 10, wherein said oligopeptide comprises 8 to 40 continuous amino acids from the sequence of the formula:

$NH_2$-W E R aa$^{63}$ T Q I A K G N E Q aa$^{73}$ F R V aa$^{77}$ L R T L L R Y Y-COOH (SEQ ID NO:35), where:

aa$^{63}$, if present, is E or I;

aa$^{73}$, if present, is S or W; and aa$^{77}$, if present, is D or N; and wherein said oligopeptide comprises at least the amino acid residues L R T L L R Y (SEQ ID NO:36).

13. A method according to claim 10, wherein X is tyrosine.

14. A method according to claim 10, wherein X is alanine.

15. A method according to claim 10, wherein said oligopeptide is a member of the group consisting of the formula:

G N E Q S F R V D L R T L L R Y X (SEQ ID NO:37); G N A Q S F R V D L R T L L R Y X (SEQ ID NO:38); G N E Q S F R V D A R T L L R Y X (SEQ ID NO:39); and G N E Q S F R V D L R T A L R Y X (SEQ ID NO:40), wherein X is an amino group to provide an amide terminal group, or the amino acids alanine or tyrosine terminating in a carboxy group.

16. An oligopeptide according to claim 9, wherein said oligopeptide comprises 8 to 40 continuous amino acids from the sequence of the formula:

$NH_2$-W E R aa$^{63}$ T Q I A K G aa$^{70}$ E Q aa$^{73}$ F R V aa$^{77}$ L R T L L R Y Y-COOH (SEQ ID NO:35)

where:

aa$^{63}$, if present, is I or E;

aa$^{70}$, if present, is N or Q;

aa$^{73}$, if present, is S or W; and aa$^{77}$, if present, is D or N.

* * * * *